US007902150B2

(12) United States Patent
Ferguson et al.

(10) Patent No.: US 7,902,150 B2
(45) Date of Patent: Mar. 8, 2011

(54) MEDICAMENTS AND PROTEINS BASED ON TGF-β MONOMERS FOR THE TREATMENT OF WOUNDS

(75) Inventors: Mark William James Ferguson, Manchester (GB); Phillip Mellors, Manchester (GB); Hugh Gerard Laverty, Manchester (GB); Nick Occleston, Manchester (GB); Sharon O'Kane, Manchester (GB); Emma Atkinson, Manchester (GB)

(73) Assignee: Renovo Limited (GB)

( * ) Notice: Subject to any disclaimer, the term of this patent is extended or adjusted under 35 U.S.C. 154(b) by 0 days.

(21) Appl. No.: 12/282,472

(22) PCT Filed: Mar. 12, 2007

(86) PCT No.: PCT/GB2007/000834
§ 371 (c)(1),
(2), (4) Date: Sep. 10, 2008

(87) PCT Pub. No.: WO2007/104946
PCT Pub. Date: Sep. 20, 2007

(65) Prior Publication Data
US 2009/0137475 A1    May 28, 2009

(30) Foreign Application Priority Data

Mar. 11, 2006  (GB) .................................. 0604966.2

(51) Int. Cl.
A61K 38/16  (2006.01)
A61K 38/17  (2006.01)
A61K 38/18  (2006.01)
(52) U.S. Cl. .......................... 514/8.9; 514/9.4; 514/21.2
(58) Field of Classification Search .................... None
See application file for complete search history.

(56) References Cited

U.S. PATENT DOCUMENTS

| | | | |
|---|---|---|---|
| 4,051,848 A | 10/1977 | Levine | |
| 5,135,915 A | 8/1992 | Czarniecki et al. | |
| 5,411,940 A | 5/1995 | Nixon et al. | |
| 5,650,494 A | 7/1997 | Cerletti et al. | |
| 5,922,846 A | 7/1999 | Cerletti et al. | |
| 5,958,411 A * | 9/1999 | Logan et al. | 424/158.1 |
| 6,054,122 A | 4/2000 | MacPhee et al. | |
| 6,057,430 A | 5/2000 | Cerletti | |
| 6,132,759 A | 10/2000 | Schacht et al. | |
| 6,331,298 B1 | 12/2001 | Ferguson et al. | |
| 6,559,123 B1 | 5/2003 | Iwata et al. | |
| 6,972,321 B1 * | 12/2005 | Hotten et al. | 530/350 |
| 7,341,994 B2 | 3/2008 | Ishikawa et al. | |
| 7,691,816 B2 | 4/2010 | Ferguson et al. | |
| 2004/0078851 A1 | 4/2004 | Huang et al. | |

FOREIGN PATENT DOCUMENTS

| | | |
|---|---|---|
| EP | 0200341 | 11/1986 |
| EP | 0 433 225 | 6/1991 |
| EP | 0 891 985 A1 * | 1/1999 |
| EP | 0 943 690 | 9/1999 |
| EP | 1 557 468 A2 | 7/2005 |
| WO | WO90/03812 | 4/1990 |
| WO | WO-91/05565 | 5/1991 |
| WO | WO93/19769 | 10/1993 |
| WO | WO-95/16034 | 6/1995 |
| WO | WO96/03432 | 2/1996 |
| WO | WO96/32131 | 10/1996 |
| WO | WO-97/05166 | 2/1997 |
| WO | WO-99/18196 | 4/1999 |
| WO | WO-00/20607 | 4/2000 |
| WO | WO-00/20612 | 4/2000 |
| WO | WO00/54797 | 9/2000 |
| WO | WO 00/56879 * | 9/2000 |
| WO | WO-01/75132 A2 | 10/2001 |
| WO | WO-01/92298 | 12/2001 |
| WO | WO-02/12336 | 2/2002 |
| WO | WO02/076494 | 10/2002 |
| WO | WO-02/099067 A2 | 12/2002 |
| WO | WO-2006/023782 | 3/2006 |
| WO | WO-2006/118617 A2 | 11/2006 |
| WO | WO-2007/007098 | 1/2007 |
| WO | WO-2007/104934 | 9/2007 |
| WO | WO-2007/104945 | 9/2007 |
| WO | WO-2008/032035 | 3/2008 |
| WO | WO-2008/032035 A1 | 3/2008 |

OTHER PUBLICATIONS

Ejima et al., "A Novel "Reverse Screening" to Identify Refolding Additives for Activin-A" Science Direct, Protein Expression and Purification, vol. 47 (2006), pp. 45-51.
Patent Cooperation Treaty (PCT) International Search Report, International Application No. PCT/GB2007/003416, completed Dec. 10, 2007, mailed Dec. 18, 2007.
U.S. Appl. No. 12/282,456—Non-Final Office Action dated Oct. 21, 2009, including Form PTO-892 (documents cited therein included by reference).
Bowie et al., "Deciphering the Message in Protein Sequences: Tolerance to Amino Acid Substitutions," Science, vol. 247, No. 4948, pp. 1306-1310 (1990).
Brannon, "Skin Anatomy," dermatology.about.com/cs/skinanatomy/a/anatomy.htm, downloaded Aug. 16, 2009.
Hao et al., TGF-β3: "A promising growth factor in engineered organogenesis," Expert Opin. Boll. Ther., vol. 8, No. 10, pp. 1485-1493 (2008).
Hirshberg, TGF—β3 in the Treatment of Pressure Ulcers: A Preliminary Report, Advances in Skin & Wound Care, vol. 14, No. 2, pp. 91-95, www.woundcarenet.com (Mar./Apr. 2001).
International Search Report for WO2007/007098 (PCT/GB2006/002577) dated Mar. 3, 2007 (4 pages).
Martin, "Wound Healing—Aiming for Perfect Skin Regeneration," Science, vol. 276, pp. 75-81 (1997).

(Continued)

Primary Examiner — Elizabeth C. Kemmerer
(74) Attorney, Agent, or Firm — McDermott Will & Emery LLP

(57) ABSTRACT

There is provided the use of monomeric TGF-βs, or there fragments or derivatives, as medicaments. These medicaments preferably comprise monomeric TGF-β3, or fragments or derivatives thereof. The medicaments provided may be used in the acceleration of wounding and/or the inhibition of scarring, in the promotion of epithelial regeneration, or in the prevention and/or treatment of fibrotic disorders.

37 Claims, 13 Drawing Sheets

OTHER PUBLICATIONS

Ngo et al., "Computational Complexity, Protein Structure Prediction, and the Levinthal Paradox," *The Protein Folding Problem and Tertiary Structure Prediction*, Merz et al, eds, Birkhauser, Boston, pp. 433-506 (1994).

Shah et al., "Neutralisation of TGF-$\beta_1$ and TGF- $\beta_2$ or exogenous addition of TGF-$\beta_3$ to cutaneous rat wounds reduces scarring," *Journal of Cell Science*, vol. 108, pp. 985-1002 (1995).

Singer et al., "Cutaneous Wound Healing," *The New England Journal of Medicine*, vol. 341, No. 10, pp. 738-746 (1999).

Tyrone et al., "Transforming Growth Factor $\beta_3$ Promotes Fascial Wound Healing in a New Animal Model," *Arch. Surg.*, vol. 135, pp. 1154-1159, www.archsurg.com, (Oct. 2000).

U.S. Appl. No. 11/995,380: File History of all prosecution documents to date, including Bibliographic Data Page and Image File Wrapper Pages from PAIR as downloaded on Aug. 13, 2010.

U.S. Appl. No. 12/282,456: Final Office Action dated May 26, 2010 (8 pages).

U.S. Appl. No. 12/282,463: File History of all prosecution documents to date, including Bibliographic Data Page and Image File Wrapper Pages from PAIR as downloaded on Aug. 21, 2010.

U.S. Appl. No. 12/440,688: File History of all prosecution documents to date, including Bibliographic Data Page and Image File Wrapper Pages from PAIR as downloaded on Aug. 13, 2010.

Vooijs et al., "Transforming growth factor-$\beta_3$—loaded microtextured membranes for skini regeneration in dermal wounds," *Journal of biomedical Materials Research*, vol. 70, No. 3, pp. 402-411 (2004).

Wang et al., "A Single Amino Acid Determines Lysophospholipid Specificity of the $S1P_1$ (EDG1) and $LPA_1$ (EDG2) Phospholipid Growth Factor Receptors," *The Journal of Biological Chemistry*, vol. 276, No. 52, pp. 49213-49220 (2001).

Wells, "Additivity of Mutational Effects in Proteins," *Biochemistry*, vol. 29, No. 37, pp. 8509-8517 (1990).

International Search Report for PCT/GB2007/00814, mailed Nov. 7, 2007.

International Search Report for PCT/GB2007/00833, mailed Mar. 14, 2008.

International Search Report for PCT/GB2007/00834, mailed Apr. 3, 2008.

O'Kane et al. "Transforming Growth Factor $\beta$s and Wound Healing" Int. J. Biochem. Cell Biol. vol. 29, No. 1, pp. 63-78 (1997).

Schmid et al. "TGF-$\beta$s and TGF-$\beta$Type II Receptor in Human Epidermis: Differential Expression in Acute and Chronic Skin Wounds" J. of Pathology, vol. 171, pp. 191-197 (993).

Vallejo et al. "Optimized procedure for renaturation of recombinant human bone morphogenetic protein-2 at high protein concentration," Biotechnology and Bioengineering, Interscience Publishers, London, GB, vol. 85, No. 6., pp. 601-609, 2004.

Vallejo et al. "Renaturation and purification of bone morphogenetic protein-2 produced as inclusion bodies in high-cell density cultures of recombinant *Escherichia coli*," J. of Biotech., Elsevier Science Publishes B.V., Amsterdam, NL vol. 94, No. 2., pp. 185-194, 2002.

\* cited by examiner

Figure 1. Comparison of Monomeric TGF-Beta 3 With Dimeric TGF-Beta 3 by SDS-PAGE (Coomassie Blue stained)
| Track | Sample | Concentration loaded per track |
|---|---|---|
| 1 | Monomeric TGF-Beta 3 | 3μg |
| 2 | Dimeric TGF-Beta 3 | 3μg |
| 3 | Invitrogen Mark 12 molecular weight standards | 10μg |
Non-Reduced Conditions         Reduced Conditions
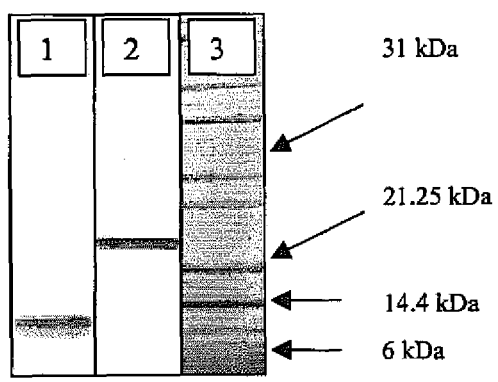
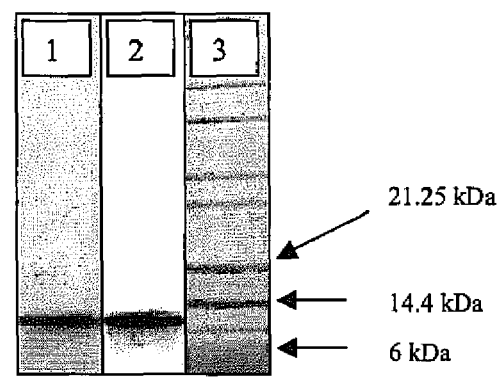

Figure 2. Template for Rat Incisional Wounding
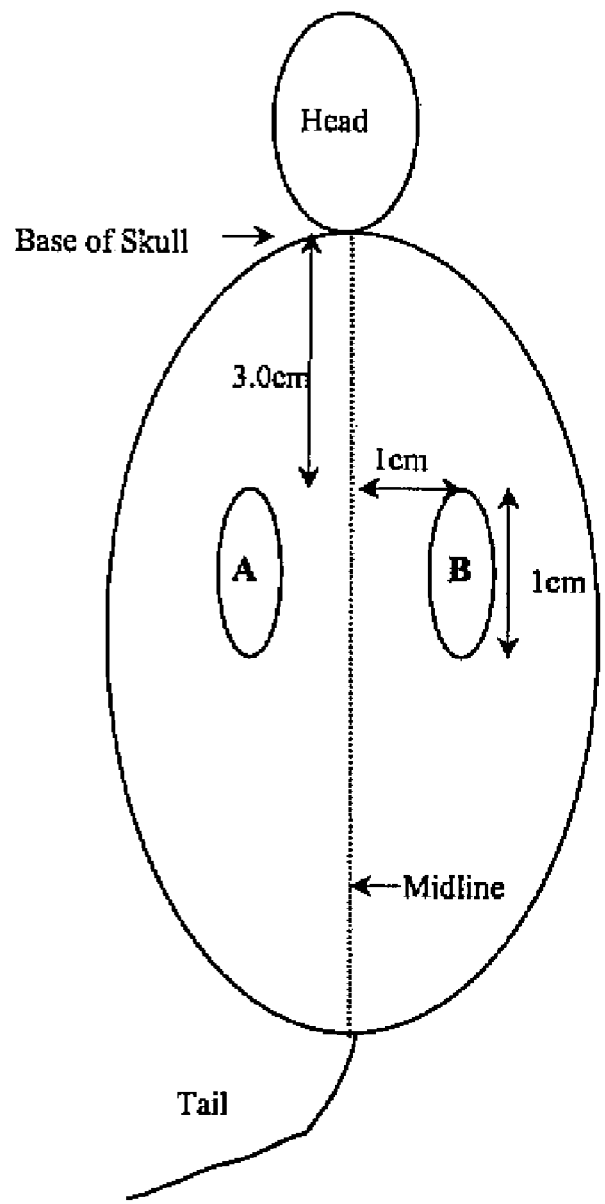

Figure 3          Wound Site Treatment.

| Group | Treatment/sample | Concentration (ng/100μL) |
|---|---|---|
| A | Monomeric 'Wild-type' TGF-Beta 3 | 50 |
| B | Monomeric 'Wild-type' TGF-Beta 3 | 100 |
| G | TGF-Beta 3 'Wild-type' Dimer | 50 |
| H | 0.25 M Maltose (Placebo control) | N/A |
| I | Naïve (no treatment control) | N/A |

Figure 4. Day 3 Mean (± SD) Macroscore for Incisional wounds (A and B) Treated with Monomeric and Dimeric 'Wild-type' TGF-Beta 3.
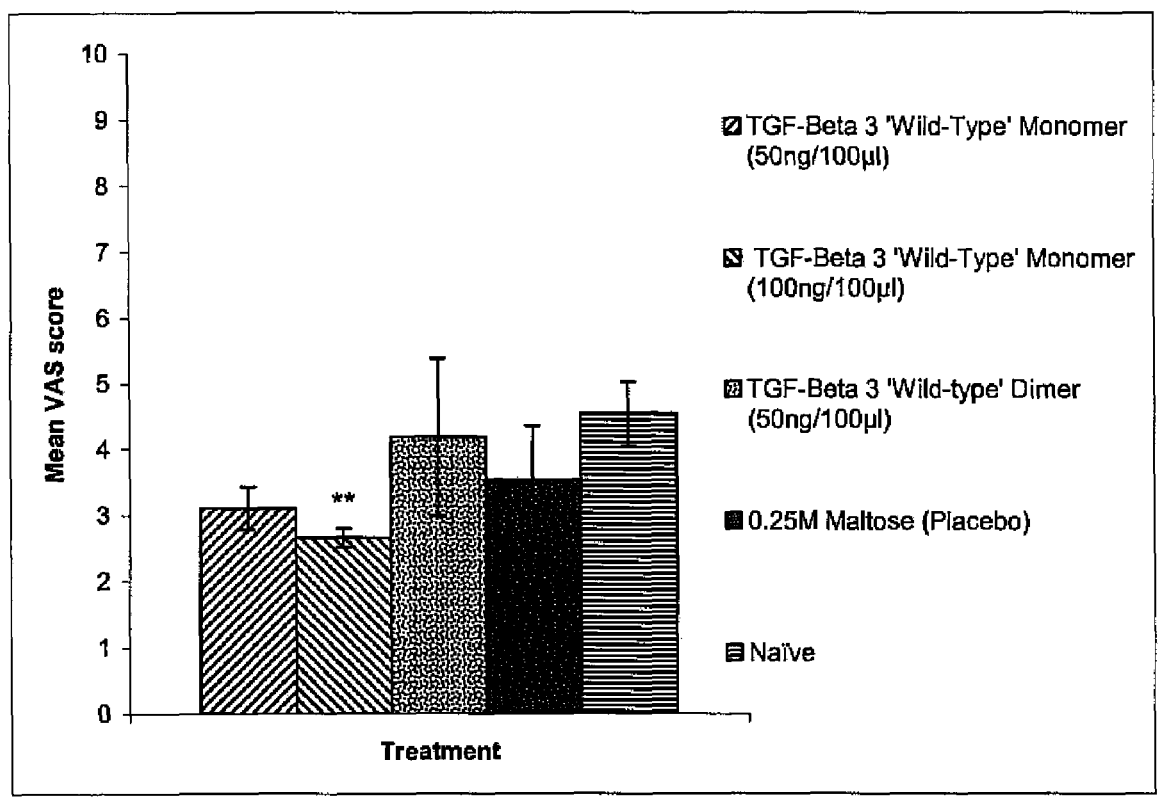
** Significantly increased healing compared to naïve wounds ($p<0.01$)

Figure 5. Wound site treatment.

| Group | Treatment/sample | Concentration (ng/100μL) |
|---|---|---|
| A | Monomeric 'Wild-type' TGF-Beta 3 | 50 |
| B | Monomeric 'Wild-type' TGF-Beta 3 | 100 |
| K | TGF-Beta 3 'Wild-type' Dimer | 50 |
| L | 0.25 M Maltose (Placebo control) | N/A |
| M | Naïve (no treatment control) | N/A |

Figure 6. Day 70 Mean (± SD) Macroscore for Incisional Wounds (A and B) Treated with Monomeric and Dimeric 'Wild-type'TGF-Beta 3.
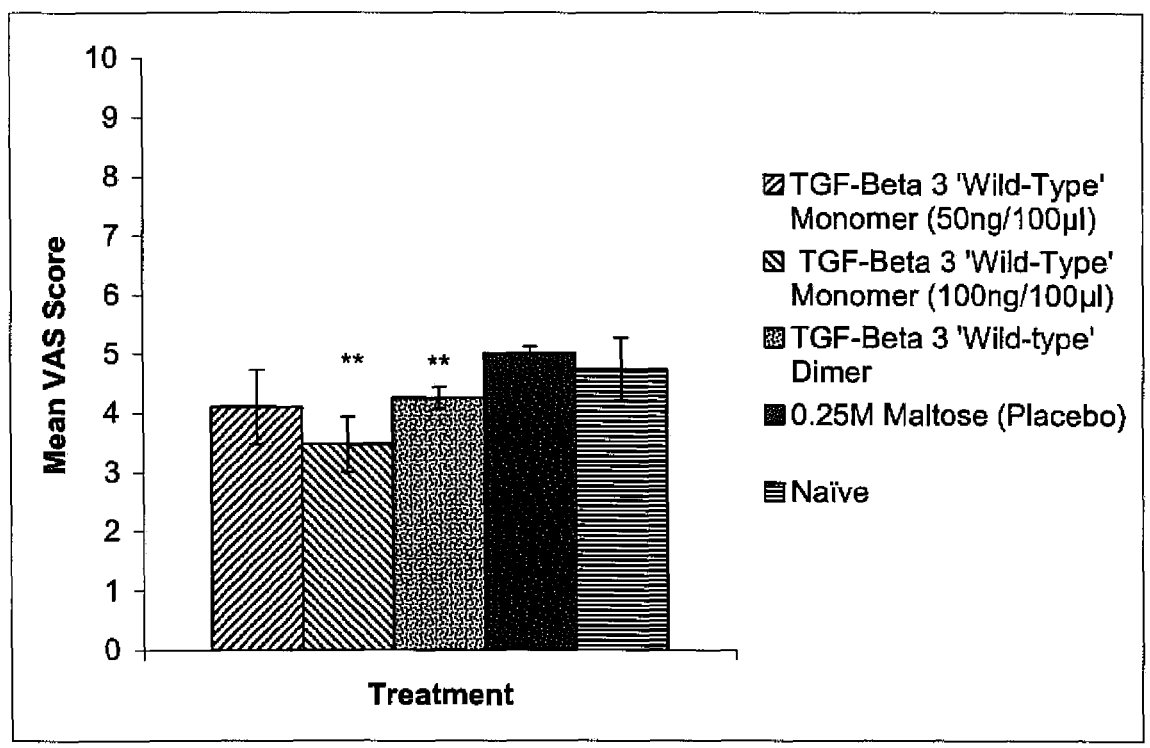
** Significantly decreased scarring compared to placebo treated wounds ($p<0.01$)

Figure 7. Representative Macroscopic Scar Images (70 days Post-Wounding).
TGF-Beta 3 'Wild-type' Monomer (50ng/100μL)
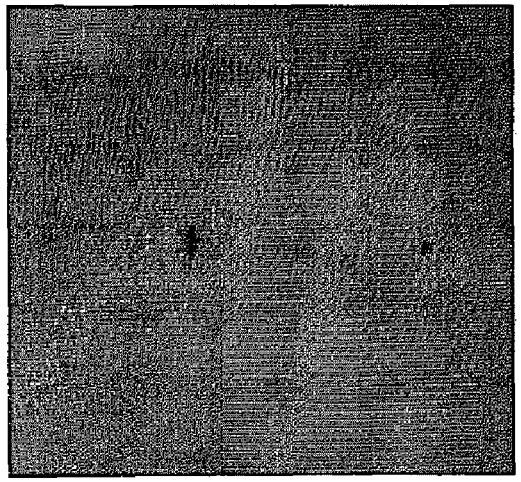
TGF-Beta 3 'Wild-type' Monomer (100ng/100μL)
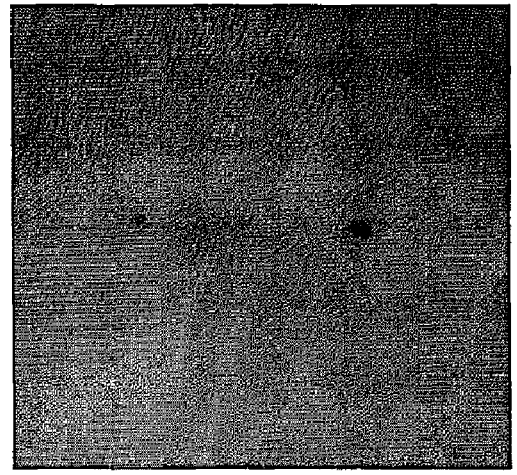
TGF-Beta 3 'Wild-type' Dimer (50ng/100μL)
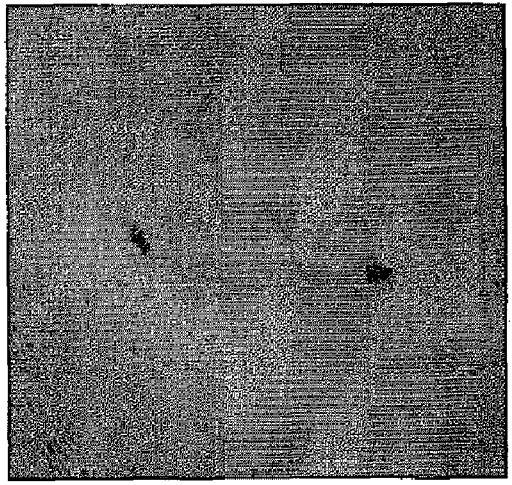
Placebo (0.25M Maltose)
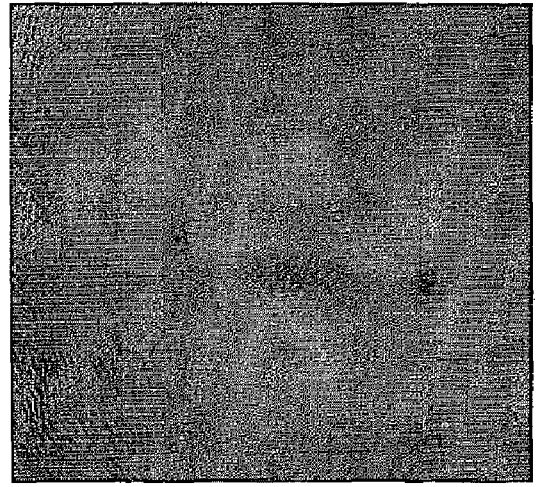

Figure 7 Cont'd. Representative Macroscopic Scar Images (70 days Post-Wounding).
Naïve
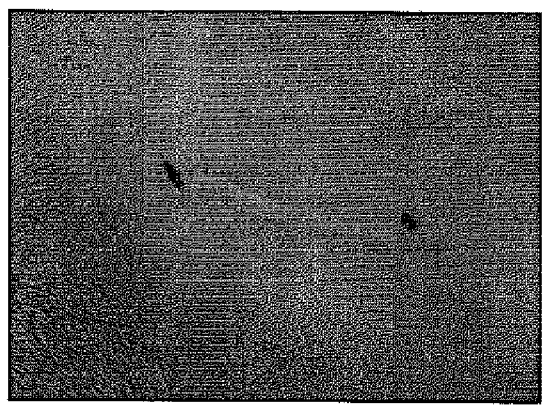

Figure 8. Representative Microscopic Scar Images of Wounds treated with Monomeric and Dimeric 'Wild-type' TGF-Beta 3 (70 days Post-Wounding).
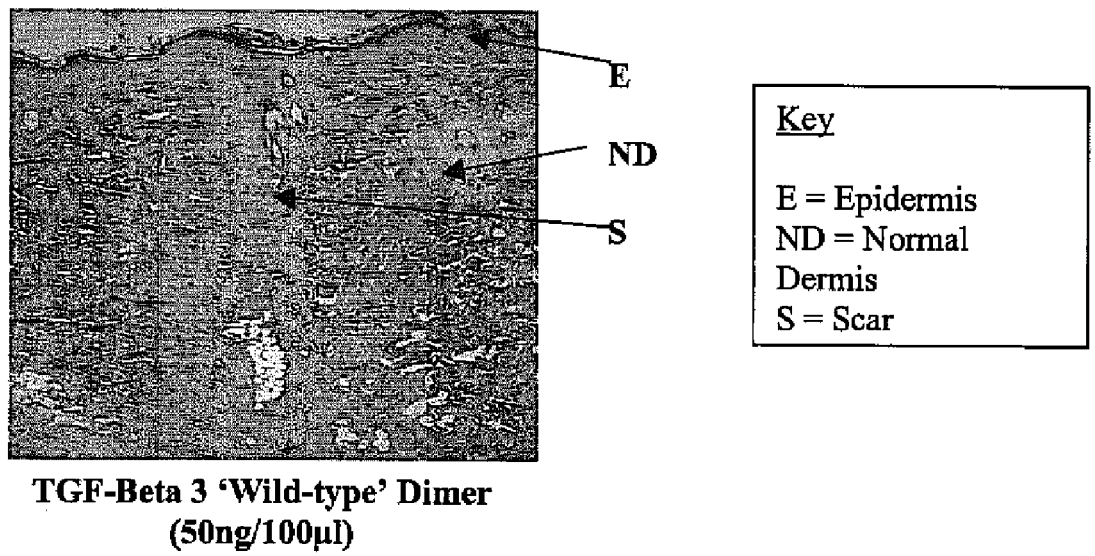
TGF-Beta 3 'Wild-type' Dimer
(50ng/100µl)
Key
E = Epidermis
ND = Normal Dermis
S = Scar

Figure 8 Cont'd. Representative Microscopic Scar Images of Wounds treated with Monomeric and Dimeric 'Wild-type' TGF-Beta 3 (70 days Post-Wounding).
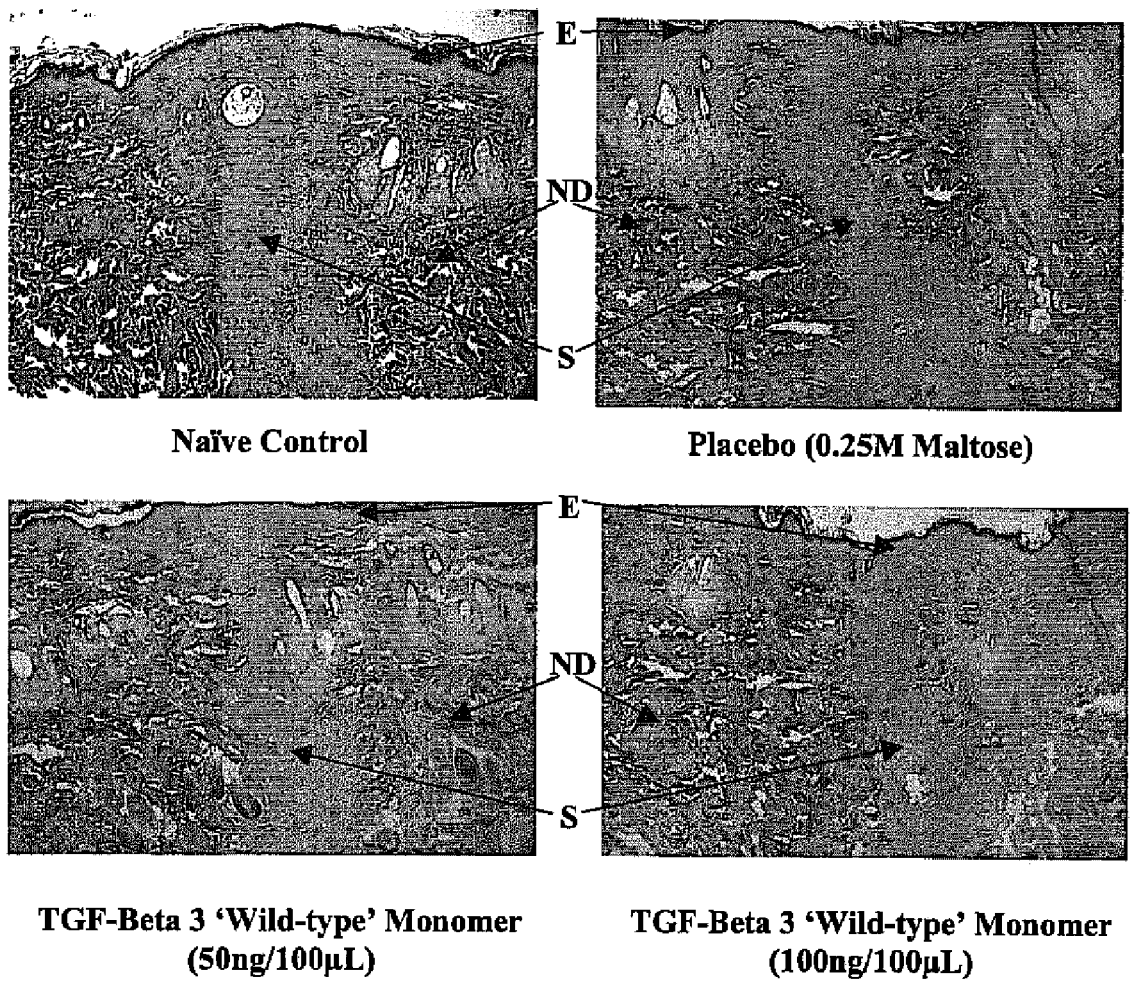

| Lane | Sample |
|---|---|
| 1 | Mark 12 Standard |
| 2 | Clone1 3hr Post-Induction (3μL) |
| 3 | Clone 2 3hr Post-Induction (3μL) |
| 4 | Clone 3 3hr Post-Induction (3μL) |
| 5 | Clone 4 3hr Post-Induction (3μL) |
| 6 | Mark 12 standard |

MEDICAMENTS AND PROTEINS BASED ON TGF-β MONOMERS FOR THE TREATMENT OF WOUNDS

CROSS-REFERENCE TO RELATED APPLICATIONS

This application is the national stage of International (PCT) Patent Application Serial No. PCT/GB2007/000834, filed Mar. 12, 2007, which claims priority to Great Britain Patent Application No. 0604966.2, filed Mar. 11, 2006; the contents of each application is incorporated herein by reference in its entirety.

The present invention relates to the provision of new medicaments. In preferred embodiments the invention provides medicaments suitable for use in the acceleration of wound healing and/or the prevention, reduction or inhibition of scarring. The invention also provides a method for the acceleration of wound healing and/or the prevention, reduction or inhibition of scarring.

The Transforming Growth Factor-Betas (TGF-βs) are a family of cytokines having diverse biological activities. The TGF-β family comprises five isoforms, TGF-β1, TGF-β2, TGF-β3, TGF-β4, and TGF-β5.

The TGF-βs have utility in many different therapeutic contexts. As a result of the therapeutic potential of TGF-βs there is much interest in the pharmaceutical application of members of the TGF-β family, particularly TGF-βs 1-3.

TGF-β1, TGF-β2 and TGF-β3 are all known to play crucial roles in the regulation of the wound healing response. TGF-β activity may influence the rate of wound healing as well as the extent of scarring that occurs as a result of healing.

TGF-β1 has uses in the prevention and/or treatment of scleroderma, angiogenesis disorders, renal disease, osteoporosis, bone disease, glomerulonephritis and renal disease.

TGF-β2 may be used in the treatment of glioma, non-small-cell lung cancer, pancreas tumour, solid tumours, colon tumour, ovary tumour, age-related macular degeneration, ocular injury, osteoporosis, retinopathy, ulcers, carcinoma, mouth inflammation and scleroderma.

TGF-β3 may be used in the treatment of fibrotic disorders, pulmonary fibrosis, liver cirrhosis, scleroderma, angiogenesis disorders, restenosis, adhesions, endometriosis, ischemic disease, bone and cartilage induction in vitro fertilisation, oral mucositis, renal disease, prevention, reduction or inhibition of scarring, enhancement of neuronal reconnection in the peripheral and central nervous system, preventing, reducing or inhibiting complications of eye surgery (such as LASIK or PRK surgery) or scarring at the back of the eye (such as scarring associated with proliferative vitreoretinopathy).

The members of the TGF-β family naturally exist in the form of dimers comprising two peptide chains. Active TGF-β dimmers have a molecular weight of approximately 25.4 kDa. The active TGF-β dimeric fragment is stabilized by hydrophobic and ionic interactions, which are further strengthened by an inter-subunit disulfide bridge. It is generally accepted that the biological activity, and so any therapeutic activity, of TGF-β family members is elicited solely by the active dimer.

In the light of the above it will be recognised that there is a well-established need to provide medicaments able to utilise the therapeutic properties of TGF-β family members. However, despite this well-recognised requirement for pharmaceutical compositions comprising TGF-β family members there are many acknowledged problems associated with the manufacture of TGF-βs for therapeutic use.

One of the greatest disadvantages of using TGF-βs as therapeutic agents is that in order to produce biologically (and so therapeutically) active protein dimers using a prokaryotic host, intensive renaturation to the biologically active dimeric form is required. Dimer formation can significantly extend the timelines of manufacture. This also has important implications in limiting the therapeutic use of any TGF-β.

It is an object of the present invention to obviate or mitigate at least some of the problems associated with prior art pharmaceutical compositions comprising TGF-βs. In particular it an object of certain embodiments of the present invention to obviate or mitigate problems associated with the use of time-intensive manufacturing approaches used to produce biologically active dimers of these proteins.

In a first aspect of the invention there is provided a TGF-β monomer, or a biologically active fragment thereof, for use as a medicament.

The invention is based on the inventors' very surprising finding that monomeric TGF-βs are able to exert biological activities that were previously believed only to be provided by dimeric TGF-β proteins. This finding makes possible the use of monomeric TGF-βs in effective medicaments capable of utilising the biological properties of a selected TGF-β. As will be immediately appreciated this finding, and hence the present invention, greatly expands the practical applications in which TGF-βs may be therapeutically used, through the reduction of time and cost associated with the manufacture of suitable medicaments.

The inventors believe that the advantages of medicaments in accordance with the invention may be provided by medicaments comprising any monomeric TGF-β isoform. Accordingly, except for where the context requires otherwise, references to TGF-β or TGF-βs may be taken to encompass any biologically active monomeric form of a TGF-β isoform such as TGF-β1, 2, 3, 4 and 5. Preferred monomers suitable for use in the medicaments of the invention are wild-type TGF-β monomers (of any desired isoform). Preferably monomeric TGF-βs suitable for use in accordance with the present invention are selected from the group consisting of TGF-β1, TGF-β2 and TGF-β3. More preferably the monomeric TGF-β is TGF-β3, and in a second aspect of the invention there is provided a TGF-β3 monomer, or a biologically active fragment thereof, for use as a medicament. It is preferred that TGF-β monomers to be used in accordance with the present invention are human TGF-β monomers. It is preferred that TGF-βs provided in medicaments in accordance with the present invention should be present in substantially entirely monomeric form. Monomeric TGF-βs suitable for use in the medicaments or methods of the invention may preferably have a molecular weight of approximately 12 kDa, and more particularly approximately 12.5 kDa.

The amino acid residue sequences of the human forms of the TGF-β1, TGF-β2 and TGF-β3 isoforms are shown as Sequence ID Nos. 1, 2 and 3 respectively, and a monomeric TGF-β comprising any of these sequences, or a biologically active fragment of any of these sequences, constitutes a preferred monomer for use in accordance with the present invention. Monomeric TGF-β3 (Sequence ID No. 3) constitutes a particularly preferred monomer for use in accordance with the various aspects of the present invention.

Except where the context requires otherwise, references in the present specification to monomeric TGF-βs (including references to particular isoforms) should be taken also to encompass biologically active fragments and derivatives of such monomeric TGF-βs. Biologically active fragments derivable from Sequence ID Nos. 1 to 3 represent preferred fragments for use in the medicaments of the invention, with biologically active fragments derivable from Sequence ID No. 3 constituting particularly preferred fragments. Preferred biologically active fragments may comprise the receptor-binding portion of the selected TGF-β isoform.

Suitable derivatives of monomeric TGF-βs that may be utilised in the medicaments or methods of the invention include: therapeutically effective peptide derivatives of monomeric TGF-βs (or their fragments); therapeutically effective fragments or derivatives comprising or based on the pharmacophore of monomeric TGF-βs (or their fragments); therapeutically effective peptoid derivatives of monomeric TGF-βs (or their fragments); therapeutically effective D-amino acid derivatives of monomeric TGF-βs (or their fragments); therapeutically effective peptidomimetics based on monomeric TGF-βs (or their fragments); therapeutically effective peptide analogues of monomeric TGF-βs (or their fragments); therapeutically effective pseudopeptides based on monomeric TGF-βs (or their fragments); therapeutically effective retro-inverso peptides based on monomeric TGF-βs (or their fragments); therapeutically effective depsipeptide derivatives based on monomeric TGF-βs (or their fragments); therapeutically effective β-peptide derivatives based on monomeric TGF-βs (or their fragments); and therapeutically effective retropeptoid derivatives based on monomeric TGF-βs (or their fragments).

The inventors have found that monomeric forms of human TGF-β3 may be used in the same way as dimeric TGF-β3, for example for the treatment of fibrotic disorders, scleroderma, angiogenesis disorders, restenosis, adhesions, endometriosis, ischemic disease, bone and cartilage induction, in vitro fertilisation, oral mucositis, renal disease, prevention, reduction or inhibition of scarring, enhancement of neuronal reconnection in the peripheral and central nervous system, preventing, reducing or inhibiting complications of eye surgery (such as LASIK or PRK surgery), treatment of cleft lip and palate, prevention, reduction or inhibition of scarring and accelerated healing of tendons and ligaments. Monomeric forms of TGF-β3 are also able to promote epithelial regeneration at sites of epithelial damage.

The inventors' findings also indicate that monomeric forms of TGF-β1 and TGF-β2 are able to exert all therapeutic activities associated with the dimeric forms of these growth factors.

"Biological activity" in the context of the present invention is preferably measured in vivo. The inventors have found that, in keeping with the findings published in the prior art, monomeric forms of TGF-βs generally do not exhibit biological activity as assessed by in vitro methods. However, in direct contrast to the prior art beliefs, the inventors have very surprisingly found that monomeric forms of TGF-βs are able to exert biological and therapeutic activity in vivo. Accordingly, it will be recognised that for a monomeric TGF-β, or a fragment or derivative thereof, to be deemed biologically active in accordance with the present invention it is not necessary for the monomeric TGF-β to exhibit biological activity measurable by both in vitro and in vivo means, but merely that it exhibits biological activity that can be measured either in vitro or in vivo, and preferably activity that can be measured in vivo.

Suitably, the biological activity of monomeric TGF-βs suitable for use in accordance with the first aspect of the invention may be measured with reference to the known biological activity of dimers of the given TGF-β. In a preferred embodiment biological activity may be measured with reference to the ability of a monomer (such as a monomer of Sequence ID No. 3) to accelerate wound healing and/or prevent, reduce or inhibit scarring.

In the light of the preceding paragraphs, it will be recognised that medicaments in accordance with the first or second aspects of the invention are particularly suitable for use in the acceleration of wound healing and/or the prevention, reduction or inhibition of scarring. Furthermore, medicaments in accordance with the first or second aspects of the invention are also particularly suitable for use in the promotion of re-epithelialisation. Indeed, in an third aspect of the invention there is provided the use of a TGF-β3 monomer, or a biologically active fragment thereof, in the preparation of a medicament for use in the acceleration of wound healing and/or the inhibition of scarring.

In a fourth aspect of the invention there is provided use of a TGF-β3 monomer, or a biologically active fragment thereof, in the preparation of a medicament for use in the promotion of epithelial regeneration.

In a fifth aspect of the invention there is provided the use of a TGFβ$_3$ monomer, or a biologically active fragment thereof in the preparation of a medicament for use in the prevention and/or treatment of a fibrotic disorder. Preferred fibrotic disorders that may be prevented and/or treated using such medicaments may be selected from the group consisting of lung fibrosis, liver fibrosis, scleroderma, skin fibrosis, muscle fibrosis, radiation fibrosis, kidney fibrosis and uterine fibrosis.

Furthermore, in a sixth aspect of the invention there is provided a method of accelerating wound healing and/or inhibiting scarring, the method comprising administering to a patient in need of such treatment a therapeutically effective amount of a monomeric TGF-β3, or a fragment thereof.

In an seventh aspect of the invention there is provided a method of promoting epithelial regeneration, the method comprising administering to a patient in need of such treatment a therapeutically effective amount of a monomeric TGF-β3, or a fragment thereof.

In an eighth aspect of the invention there is provided a method of preventing and/or treating a fibrotic disorder, the method comprising administering to a patient in need of such prevention and/or treatment a therapeutically effective amount of a monomeric TGF-β3, or a fragment thereof. Preferred fibrotic disorders that may be prevented and/or treated using such methods may be selected from the group consisting of lung fibrosis, liver fibrosis, scleroderma, skin fibrosis, muscle fibrosis, radiation fibrosis, kidney fibrosis and uterine fibrosis For the purposes of the present invention a therapeutically effective amount of a monomeric TGF-β, or a fragment thereof, is an amount sufficient to bring about a required:

i) acceleration in wound healing and/or inhibition of scarring; or ii) promotion of epithelial regeneration; or iii) prevention and/or treatment of a fibrotic disorder.

The extent of acceleration of wound healing and/or inhibition of scarring, or epithelial regeneration, or prevention or reduction of fibrosis that may be required will be apparent to, and indeed may readily be determined by, a clinician responsible for the care of the patient. A suitable assessment of the extent of acceleration of wound healing and/or the inhibition of scarring, or promotion of epithelial regeneration, or the prevention or reduction of fibrosis may be determined by the clinician, and may be with reference to suggested methods of measurement described herein.

Suitable and preferred monomeric TGF-βs for use in accordance with the invention may be selected with reference to any or all of the considerations described herein.

In the case where it is wished to effect accelerated wound healing with prevention, reduction or inhibition of scarring or to effect the prevention or treatment of fibrotic disorders e.g pulmonary fibrosis, liver cirrhosis, scleroderma, glomerulonephritis, or the like, it will generally be preferred to use monomeric TGF-β3 or a suitable biologically active fragment.

Although the use of monomeric TGF-β3 has particularly notable benefits, medicaments comprising monomeric forms of other TGF-β isoforms also have great value.

For example, medicaments comprising monomeric TGF-β1, or biologically active fragments thereof, may have uses in the prevention and/or treatment of chronic non healing wounds e.g. venous ulcers, pressure sores, diabetic ulcers, angiogenesis disorders, renal disease, osteoporosis, bone disease, glomerulonephritis and renal disease. By way of example, locally delivered, wild type dimeric TGF-β1 has been shown in animal models to be a potent stimulator of bone growth and regeneration. Furthermore, administration of TGF-β1 has been shown to protect tissues from ischemia-reperfusion injury, particularly in the brain (following stroke), and in the heart (following coronary artery occlusion).

Medicaments comprising monomeric TGF-β2, or biologically active fragments thereof, may be used in the treatment of glioma, non-small-cell lung cancer, pancreas tumour, solid tumours, colon tumour, ovary tumour, age-related macular degeneration, ocular injury, osteoporosis, retinopathy, ulcers, carcinoma, mouth inflammation and scleroderma. By way of example, topical application of wild type dimeric TGF-β2 has been shown in two clinical trials to accelerate the closure of chronic leg ulcers associated with venous stasis; and local delivery of recombinant human TGF-β2 in animal models has been shown to promote bone re-growth and regeneration.

Medicaments comprising monomeric TGF-β3, or biologically active fragments thereof, may be used in the treatment of wounds (including chronic wounds such as ulcers), scleroderma, fibrotic disorders e.g. pulmonary fibrosis, liver cirrhosis, kidney fibrosis etc., angiogenesis disorders, restenosis, adhesions, endometriosis, ischemic disease, bone and cartilage induction, in vitro fertilisation, oral mucositis and renal disease. By way of example, topical application of wild type, dimeric TGF-β3 has been shown, in animal models and the clinic, to accelerate the healing rate of chronic, non-healing pressure ulcers; reduce the incidence, severity, and duration of oral mucositis; and reduce the adverse side effects of radiation gastro-intestinal syndrome resulting from damage to stem cells caused by radiotherapy and chemotherapy during cancer treatment. The inventors' findings indicate that monomeric TGF-β3 may be used in all of these contexts in order to bring about the known therapeutic activities of dimeric TGF-β3.

The ability of certain methods and medicaments of the invention (such as those utilising TGF-β monomers as set out in Sequence ID No. 3) to accelerate the healing of wounds may be readily appreciated and/or measured with reference to properties exhibited by treated wounds. For present purposes a "treated wound" may be considered to be a wound exposed to a therapeutically effective amount of a medicament of the invention, or which has received treatment in accordance with the methods of the invention.

Acceleration of the healing of treated wounds may be illustrated by an increased rate of epithelialisation as compared to control wounds. Thus the methods and medicaments of the invention promote a more rapid re-constitution of a functional epithelial layer over a wounded area than would otherwise be the case.

Alternatively or additionally, accelerated healing of treated wounds may be illustrated by decreased width compared to control wounds at comparable time points. It will be appreciated that this reduction in wound width ensures that there is a relatively faster rate of wound closure (since there is less width of wound to be closed) and is indicative of the ability of such medicaments to accelerate the healing response. Narrower wounds may result in narrower scars that are aesthetically preferable to wider scars Accordingly, accelerated wound healing in the context of the present invention should be taken to encompass any increase in the rate of healing of a treated wound as compared with the rate of healing occurring in control-treated or untreated wounds. Preferably the acceleration of wound healing may be assessed with respect to either comparison of the rate of re-epithelialisation achieved in treated and control wounds, or comparison of the relative width of treated and control wounds at comparable time points. More preferably accelerated wound healing may be defined as comprising both an increased rate of re-epithelialisation and a reduction of wound width compared to control wounds at comparable time points.

Preferably the promotion of accelerated wound healing may give rise to a rate of wound healing that is at least 5%, 10%, 20% or 30% greater than the rate of healing occurring in a control or untreated wound. More preferably the promotion of accelerated wound healing may give rise to a rate of healing that is at least 40%, 50% or 60% greater than healing in a control wound. It is even more preferred that promotion of accelerated wound healing may give rise to a rate of healing that is at least 70%, 80%, or 90% greater than that occurring in control wounds, and most preferably the promotion of accelerated wound healing may give rise to a rate of healing that is at least 100% greater than the rate occurring in control wounds.

There exist a wide range of wound healing disorders that are characterised, or at least partially characterised, by inappropriate failure, delay or retardation of the normal wound healing response. The ability of certain methods and medicaments of the invention to promote accelerated wound healing are thus of utility in the prevention or treatment of such disorders.

Since certain methods and medicaments of the invention are able to bring about the acceleration of wound healing through the promotion of a stimulated re-epithelialisation response (thereby increasing the rate at which the wound closes) it will be appreciated that these methods and medicaments of the invention are particularly advantageous for treatment of wounds of patients that may otherwise be prone to defective, delayed or otherwise impaired re-epithelialisation. For example, it is well known that dermal wounds in the aged exhibit a less-vigorous re-epithelialisation response than do those of younger individuals. There are also many other conditions or disorders in which wound healing is associated with delayed or otherwise impaired re-epithelialisation. For example patients suffering from diabetes, patients with polypharmacy (for example as a result of old age), post-menopausal women, patients susceptible to pressure injuries (for example paraplegics), patients with venous disease, clinically obese patients, patients receiving chemotherapy, patients receiving radiotherapy, patients receiving steroid treatment or immuno-compromised patients may all suffer from wound healing with impaired re-epithelialisation. In many such cases the lack of a proper re-epithelialisation response contributes to the development of infections at the wound site, which may in turn contribute to the formation of chronic wounds such as ulcers. Accordingly it will be appreciated that such patients are particularly likely to benefit from suitable methods or medicaments of the invention.

Chronic wounds are perhaps the most important example of disorders associated with a delayed wound healing response. A wound may be defined as chronic if it does not show any healing tendency within eight weeks of formation when subject to appropriate (conventional) therapeutic treatment. Well-known examples of chronic wounds include venous ulcers, diabetic ulcers and decubitus ulcers, however chronic wounds may arise from otherwise normal acute injuries at any time. Typically chronic wounds may arise as a result of infection of the wound site, inadequate wound treatment, or as a sequitur of progressive tissue breakdown caused by venous, arterial, or metabolic vascular disease, pressure, radiation damage, or tumour.

It will be appreciated that methods and medicaments of the invention capable of accelerating wound healing may be utilised in the treatment of existing chronic wounds in order to promote their healing. Such methods and medicaments may promote the re-epithelialisation of chronic wounds, thereby bringing about healing and closure of the disorder. Preferred methods and medicaments of the invention (such as those utilising monomeric TGF-$\beta$ comprising Sequence ID No. 3) may also inhibit scarring associated with wound healing. The prevention of scarring in such contexts may be particularly advantageous since chronic wounds may typically extend over relatively large portions of a patient's body.

In addition, or alternatively, to their use in the treatment of existing chronic wounds, suitable methods and medicaments of the invention may be used to prevent acute wounds of patients predisposed to impaired wound healing developing into chronic wounds. Since suitable methods and medicaments of the invention are able to promote epithelial coverage of the damaged site they are able to reduce the likelihood of a treated wound becoming infected. Similarly, this promotion of re-epithelialisation may be of benefit in the treatment of chronic wounds arising as a result of other conditions such as diabetes or venous disease.

A further group of patients that may derive particular benefit from the methods and medicaments of the invention are those in which the immune system is compromised (for example patients undergoing chemotherapy or radiotherapy, or those suffering from HIV infection). It is well recognised that wounds of immunocompromised patients, who may be unable to mount a normal inflammatory response after wounding, tend to be associated with poor healing outcomes. Such patients may benefit from treatment with suitable methods and medicaments of the invention.

The ability of medicaments and methods of the invention utilising monomeric TGF-$\beta$s comprising Sequence ID No. 3 to promote accelerated wound healing while preventing, reducing or inhibiting scarring is also of use in more general clinical contexts. Examples of these further benefits may be considered with reference to the healing of wounds by primary, secondary or tertiary intention, as described below.

For the purposes of the present invention, healing by primary intention may be considered to involve the closure by surgical means (such as sutures, adhesive strips or staples) of opposing edges of a wound. Healing by primary intention is typically employed in the treatment of surgical incisions or other clean wounds, and is associated with minimal levels of tissue loss. The skilled person will recognise that since suitable medicaments or methods in accordance with the invention (such as those utilising monomers comprising Sequence ID No. 3) are capable of reducing wound width they also facilitate the joining of opposing wound edges, and thus may be beneficial in wound healing by primary intention. Furthermore, such methods or medicaments may (as described further below) result in the prevention, reduction or inhibition of scarring that may otherwise occur on such healing. The inventors believe that treatment in this manner may have an impact on both the macroscopic and microscopic appearance of scars formed from treated wounds; macroscopically the scars may be less noticeable and blend with the surrounding skin, microscopically the scars may exhibit a regeneration of a more normal skin structure.

For the purposes of the present invention healing by secondary intention may be considered to constitute the closure of wounds by the wound healing process, without direct surgical intervention. Wounds to be healed by secondary intention may be subject to continued care (for example the dressing and re-dressing of the wound as well as the application of suitable medicaments), but it is the natural processes of granulation tissue formation and re-epithelialisation that bring about the closure of the wound. It will be appreciated that since preferred medicaments and methods of the invention (such as those utilising monomers comprising Sequence ID No. 3) are able to increase the rate of re-epithelialisation and decrease subsequent scarring as compared to that occurring in control wounds they have utility in the promotion of wound healing by secondary intention.

Healing by tertiary intention may be considered to comprise the surgical closure of a wound that has previously been left open to allow at least partial granulation tissue formation and re-epithelialisation. The properties of preferred methods and medicaments of the invention that make them suitable for use in healing by primary or secondary intention are also beneficial in the context of promoting wound healing by tertiary intention.

The use of preferred methods and medicaments of the invention utilising monomers comprising Sequence ID No. 3 to stimulate re-epithelialisation (as part of their promotion of accelerated wound healing) while inhibiting scarring is also particularly effective in the treatment of wounds associated with grafting procedures. Treatment using such methods and medicaments of the invention is of benefit both at a graft donor site (where it can aid the re-establishment of a functional epithelial layer while preventing, reducing or inhibiting scar formation), and also at graft recipient sites (where the anti-scarring effects of the treatment inhibit scar formation, while the accelerated healing promotes integration of the grafted tissue). The inventors believe that the methods and medicaments of the invention confer advantages in the contexts of grafts utilising skin, artificial skin, or skin substitutes.

The inventors have found that the methods and medicaments of the invention utilising monomers comprising Sequence ID No. 3 are able to promote accelerated wound healing with inhibition of scarring when administered either prior to wounding, or once a wound has already been formed.

The inventors have found that methods or medicaments of the invention utilising monomeric TGF-$\beta$3s, such as those comprising Sequence ID No. 3, are capable of promoting epithelial regeneration. The promotion of epithelial regeneration within the context of the present invention may be understood to encompass any increase in the rate of epithelial regeneration as compared to the regeneration occurring in a control-treated or untreated epithelium.

The rate of epithelial regeneration attained using suitable methods or medicaments in accordance with the invention may readily be compared with that taking place in control-treated or untreated epithelia using any suitable model of epithelial regeneration known in the art. For example, the rate at which sites of experimental epithelial damage having known areas regenerate may be compared using well known in vivo models in mice, rats, rabbits or pigs such as those described in Tomlinson and Ferguson (2003), Davidson et al. (1991) and Paddock et al. (2003).

Without wishing to be bound by any hypothesis the inventors believe that the promotion of epithelial regeneration achieved by monomeric forms of TGF-β3 is mediated by the monomers' promotion of epithelial cell migration. The epithelial cells (the migration of which has been promoted) are thereby able to re-populate and regenerate the damaged epithelium more rapidly than occurs in the absence of treatment.

It will be appreciated that promotion of epithelial regeneration using monomers comprising Sequence ID No. 3 may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in patients suffering from epithelial damage.

There are many contexts in which the body's re-epithelialisation response may be defective. For example, defective re-epithelialisation in the skin is associated with conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

As has been set out above, certain methods or medicaments in accordance with the present invention (and particularly those utilising monomers comprising Sequence ID No. 3) are able to prevent, reduce or otherwise inhibit scarring. This inhibition of scarring can be effected at any body site and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may improve the macroscopic and microscopic appearance of scars; macroscopically the scars may be less visible and blend with the surrounding skin, microscopically the collagen fibres within the scar may have morphology and organisation that is more similar to those in the surrounding skin. The prevention, reduction or inhibition of scarring within the context of the present invention should be understood to encompass any degree of prevention, reduction or inhibition in scarring as compared to the level of scarring occurring in a control-treated or untreated wound (as defined elsewhere in the specification). Except where the context requires otherwise references to "prevention", "reduction" or "inhibition" of scarring may be taken to be equivalent mechanisms that are all manifested in anti-scarring activity.

The prevention, reduction or inhibition of dermal scarring achieved using methods and medicaments of the invention may be assessed and/or measured with reference to either the microscopic or, preferably, macroscopic appearance of a treated scar as compared to the appearance of an untreated scar. More preferably the prevention, reduction or inhibition of scarring may be assessed with reference to both macroscopic and microscopic appearance of a treated scar. For the present purposes a "treated scar" may be defined as a scar formed on healing of a treated wound, whereas an "untreated scar" may be defined as the scar formed on healing of an untreated wound, or a wound treated with placebo or standard care. Suitable comparison scars may preferably be matched to the treated scar with reference to scar age, site, size and patient.

In considering the macroscopic appearance of a scar resulting from a treated wound, the extent of scarring, and hence the magnitude of any prevention, inhibition or reduction in scarring achieved, may be assessed with reference to any of a number of parameters.

Suitable parameters for the macroscopic assessment of scars may include:

i) Colour of the scar. As noted above, scars may typically be hypopigmented or hyperpigmented with regard to the surrounding skin. Inhibition or reduction of scarring may be demonstrated when the pigmentation of a treated scar more closely approximates that of unscarred skin than does the pigmentation of an untreated scar. Similarly, scars may be redder than the surrounding skin. In this case inhibition or reduction of scarring may be demonstrated when the redness of a treated scar fades earlier, or more completely, or to resemble more closely the appearance of the surrounding skin, compared to an untreated scar.

ii) Height of the scar. Scars may typically be either raised or depressed as compared to the surrounding skin. Inhibition or reduction of scarring may be demonstrated when the height of a treated scar more closely approximates that of unscarred skin (i.e. is neither raised nor depressed) than does the height of an untreated scar.

iii) Surface texture of the scar. Scars may have surfaces that are relatively smoother than the surrounding skin (giving rise to a scar with a "shiny" appearance) or that are rougher than the surrounding skin. Inhibition or reduction of scarring may be demonstrated when the surface texture of a treated scar more closely approximates that of unscarred skin than does the surface texture of an untreated scar.

iv) Stiffness of the scar. The abnormal composition and structure of scars means that they are normally stiffer than the undamaged skin surrounding the scar. In this case, inhibition or reduction of scarring may be demonstrated when the stiffness of a treated scar more closely approximates that of unscarred skin than does the stiffness of an untreated scar.

A treated scar will preferably demonstrate prevention, inhibition or reduction of scarring as assessed with reference to at least one of the parameters for macroscopic assessment set out above. More preferably a treated scar may demonstrate prevented, inhibited or reduced scarring with reference to at least two of the parameters, even more preferably at least three of the parameters, and most preferably all four of these parameters. An overall assessment of scarring may be made using, for example, a Visual Analogue Scale or a digital assessment scale.

Suitable parameters for the microscopic assessment of scars may include:

i) Thickness of extracellular matrix (ECM) fibres. Scars typically contain thinner ECM fibres than are found in the surrounding skin. This property is even more pronounced in the case of keloid and hypertrophic scars. Inhibition or reduction of scarring may be demonstrated when the thickness of ECM fibres in a treated scar more closely approximates the thickness of ECM fibres found in unscarred skin than does the thickness of fibres found in an untreated scar.

ii) Orientation of ECM fibres. ECM fibres found in scars tend to exhibit a greater degree of alignment with one another than do those found in unscarred skin (which have a random orientation frequently referred to as "basket weave"). The ECM of pathological scars such as keloids and hypertrophic scars may exhibit even more anomalous orientations, frequently forming large "swirls" or "capsules" of ECM molecules. Accordingly, inhibition or reduction of scarring may be demonstrated when the orientation of ECM fibres in a treated scar more closely approximates the orientation of ECM fibres found in unscarred skin than does the orientation of such fibres found in an untreated scar.

iii) ECM composition of the scar. The composition of ECM molecules present in scars shows differences from that found in normal skin, with a reduction in the amount of elastin present in ECM of scars. Thus inhibition or reduction of scarring may be demonstrated when the composition of ECM fibres in the dermis of a treated scar more closely approximates the composition of such fibres found in unscarred skin than does the composition found in an untreated scar.

iv) Cellularity of the scar. Scars tend to contain relatively fewer cells than does unscarred skin. It will therefore be appreciated that inhibition or reduction of scarring may be demonstrated when the cellularity of a treated scar more closely approximates the cellularity of unscarred skin than does the cellularity of an untreated scar.

A treated scar will preferably demonstrate prevention, reduction or inhibition of scarring as assessed with reference to at least one of the parameters for microscopic assessment set out above. More preferably a treated scar may demonstrate prevention, reduction or inhibition of scarring with reference to at least two of the parameters, even more preferably at least three of the parameters, and most preferably all four of these parameters.

Prevention, reduction or inhibition of scarring of a treated wound may further be assessed with reference to suitable parameters used in the:

i) macroscopic clinical assessment of scars, particularly the assessment of scars upon a subject;
ii) assessment of photographic images of scars;
iii) assessment of silicone moulds or positive plaster casts made from silicone moulds of scars; and
iv) microscopic assessment of scars, for example by histological analysis of the microscopic structure of scars.

It will be appreciated that prevention, reduction or inhibition of scarring of a treated wound may be indicated by improvement of one or more of such suitable parameters, and that in the case of prevention, reduction or inhibition as assessed with reference to a number of parameters that these parameters may be combined from different assessment schemes (e.g. reduction, inhibition or improvement in at least one parameter used in macroscopic assessment and at least one parameter used in microscopic assessment).

Prevention, reduction or inhibition of scarring may be demonstrated by an improvement in one or more parameters indicating that a treated scar more closely approximates unscarred skin with reference to the selected parameter(s) than does an untreated or control scar.

Suitable parameters for the clinical measurement and assessment of scars may be selected based upon a variety of measures or assessments including those described by Beausang et al (1998) and van Zuijlen et al (2002).

Typically, suitable parameters may include:

1. Assessment with Regard to Visual Analogue Scale (VAS) Scar Score.

Prevention, reduction or inhibition of scarring may be demonstrated by a reduction in the VAS score of a treated scar when compared to a control scar. A suitable VAS for use in the assessment of scars may be based upon the method described by Beausang et al (1998).

2. Scar Height, Scar Width, Scar Perimeter, Scar Area or Scar Volume.

The height and width of scars can be measured directly upon the subject, for example by use of manual measuring devices such as callipers. Scar width, perimeter and area may be measured either directly on the subject or by image analysis of photographs of the scar. The skilled person will also be aware of further non-invasive methods and devices that can be used to investigate suitable parameters, including silicone moulding, ultrasound, optical three-dimensional profilimetry and high resolution Magnetic Resonance Imaging.

Prevention, reduction or inhibition of scarring may be demonstrated by a reduction in the height, width, area or volume, or any combination thereof, of a treated scar as compared to an untreated scar.

3. Appearance and/or Colour of Scar Compared to Surrounding Unscarred Skin.

The appearance or colour of a treated scar may be compared to that of surrounding unscarred skin, and the differences (if any) compared with the difference between the appearance and colour of untreated scars and unscarred skin. Such a comparison may be made on the basis of a visual assessment of the respective scars and unscarred skin. The appearance of a scar may be compared with unscarred skin with reference to whether the scar is lighter or darker than the unscarred skin. The respective colours of the scars and skin may be perfectly matched to one another, slightly mismatched, obviously mismatched or grossly mismatched.

Alternatively or additionally to visual assessment, there are a number of non-invasive colourimetry devices which are able to provide data with respect to pigmentation of scars and unscarred skin, as well as redness of the skin (which may be an indicator of the degree of vascularity present in the scar or skin). Examples of such devices include the Minolta Chronameter CR-200/300; Labscan 600; Dr. Lange Micro Colour; Derma Spectrometer; laser-Doppler flow meter; and Spectrophotometric intracutaneous Analysis (SIA) scope.

Prevention, reduction or inhibition of scarring may be demonstrated by a smaller magnitude of difference between the appearance or colour of treated scars and unscarred skin than between untreated scars and unscarred skin.

4. Scar Distortion and Mechanical Performance

Scar distortion may be assessed by visual comparison of a scar and unscarred skin. A suitable comparison may classify a selected scar as causing no distortion, mild distortion, moderate distortion or severe distortion.

The mechanical performance of scars can be assessed using a number of non-invasive methods and devices based upon suction, pressure, torsion, tension and acoustics. Suitable examples include of known devices capable of use in assessing mechanical performance of scars include Indentometer, Cutometer, Reviscometer, Visco-elastic skin analysis, Dermaflex, Durometer, Dermal Torque Meter, Elastometer.

Prevention, reduction or inhibition of scarring may be demonstrated by a reduction in distortion caused by treated scars as compared to that caused by untreated scars. It will also be appreciated that prevention, reduction or inhibition of scarring may be demonstrated by the mechanical performance of unscarred skin being more similar to that of treated scars than of untreated scars.

5. Scar Contour and Scar Texture

Scar contour may be investigated by means of visual assessment. Suitable parameters to consider in such an assessment include whether or not a scar is flush with surrounding skin, slightly proud, slightly indented, hypertrophic or keloid. The texture of a scar may be assessed with reference to the scar's appearance, and this may also be undertaken by a visual assessment as to whether the scar is, for instance, matt or shiny or has a roughened or smooth appearance as compared to unscarred skin.

Scar texture may additionally be assessed with reference to whether the scar has the same texture as unscarred skin (normal texture), is just palpable, firm or hard compared to unscarred skin. The texture of scars may also be assessed with reference to the Hamilton scale (described in Crowe et al, 1998).

In addition to the techniques set out above, there are a number of non-invasive profilimetry devices that use optical or mechanical methods for assessment of scar contour and/or texture. Such assessments may be carried out on the body of the subject or, for example, on silicone mould impressions of scars, or on positive casts made from such impressions.

Prevention, reduction or inhibition of scarring may be demonstrated in the event that treated scars have scar profiles and textures more comparable to unscarred skin than do untreated scars.

Photographic Assessments

Independent Lay Panel

Photographic assessment of treated and untreated scars may be performed by an independent lay panel of assessors using standardised and calibrated photographs of the scars. The scars may be assessed by an independent lay panel to provide categorical ranking data (e.g. that a given treated scar is "better", "worse" or "no different" when compared to an untreated scar) and quantitative data using a Visual Analogue Scale (VAS) based upon the method described by Beausang et al (1998). The capture of these data may make use of suitable software and/or electronic system(s) as described in the applicant's co-pending patent application.

Expert Panel

Photographic assessment of treated and untreated scars may alternatively or additionally be performed by a panel of expert assessors using standardised and calibrated photographs of the scars to be assessed. The panel of experts may preferably consist of suitable individuals skilled in the art such as plastic surgeons and scientists of suitable backgrounds.

Such assessment may provide categorical data, as described above or with respect to the comparison of a time-course of images of selected treated and untreated scars.

Suitable assessments to be made may include:

Identification of the best scar, which for the purposes of the present invention may be considered that scar which most closely resembles the surrounding skin. Once the best scar has been identified the magnitude of the difference between scars may be considered, for example is the difference between scars slight or obvious. Further parameters that may be considered include the earliest time after scar formation at which a difference between scars may be detected, the time post-formation at which the difference between scars is most obvious (or alternatively the finding that the difference continues after the last timepoint assessed), as well as considering whether or not the better scar remains consistently better.

Consideration may also be given to whether or not one scar is consistently redder than the other, and whether the redness fades over the timepoints considered (or continues after the last timepoint) and if so at what time after scar formation. An expert panel may also consider at what time after formation any difference in redness becomes detectable, as well as the time post-formation at which the difference in redness is most obvious.

An expert panel may also consider whether or not one of a treated or untreated scar is consistently whiter than the other, or whiter than unscarred skin. In the event that a difference in whiteness is detectable consideration may be given to the time after scar formation at which the difference may be detected, the time at which the difference is most obvious, and the time at which the difference disappears.

A further parameter that may be assessed by an expert panel is the texture of treated and untreated scars. In comparing treated and untreated scars the expert panel may consider which of the scars has the best skin texture, the earliest time after scar formation at which any difference present may be detected, the time post formation at which any difference is most obvious, and the time at which any difference disappears Comparison of treated and untreated scars may further assess which of the scars is narrowest, and which of the scars is shortest. Consideration may also be given to the shape of the scar and the proportion of the scar margin that is distinguishable from the surrounding skin. As with previously described visual assessments and assessments of colour the presence, degree and location of hyper-pigmentation may also be considered.

As noted above, one of the ways in which the quality of treated and untreated scars may be compared is by microscopic assessment. Microscopic assessment of scar quality may typically be carried out using histological sections of scars. The process of microscopically assessing and measuring scars may take into consideration categorical data based on the following suitable parameters:

1. Epidermal restitution. Particular attention may be paid to the degree of restoration of the rete ridges, and to the thickness of the restored epidermis.

2. Angiogenesis and Inflammation. Consideration may be given to the number of blood vessels present, the size of the blood vessels present and evidence of inflammation, including an assessment of any level of inflammation present.

3. Collagen organisation. In assessing collagen organisation reference may be made to the orientation of collagen fibres present in the scar, the density of such fibres and collagen fibre thickness in the papillary and reticular dermis.

4. Visual analogue scale (VAS) assessment of collagen organisation for the papillary dermis and for the reticular dermis may also provide a useful index of scar quality.

5. Other features that may be taken into account in assessing the microscopic quality of scars include elevation or depression of the scar relative to the surrounding unscarred skin, and the prominence or visibility of the scar at the normal dermal interface.

6. It will be seen that the assessments described above allow the generation of scar ranking data which is able to provide an indication as to whether a treated scar is better, worse or no different compared to a control, untreated or other suitable comparator scar.

In addition to categorical data, quantitative data (preferably relating to the above parameters) can be generated using image analysis in combination with suitable visualisation techniques. Examples of suitable visualisation techniques that may be employed in assessing scar quality are specific histological stains or immuno-labelling, wherein the degree of staining or labelling present may be quantitatively determined by image analysis Quantitative data may be usefully and readily produced in relation to the following parameters:
1. Scar width, height, elevation, volume and area.
2. Epithelial thickness and coverage (for example the area of epidermis present in a scar or the proportion of a wound with epidermal coverage).
3. Number, size, area (i.e. cross-section) and location of blood vessels.
4. Degree of inflammation, number, location and populations/types of inflammatory cells present.
5. Collagen organisation, collagen fibre thickness, collagen fibre density.

Prevention, reduction or inhibition of scarring may be demonstrated by a change in any of the parameters considered above such that a treated scar more closely resembles unscarred skin than does a control or untreated scar (or other suitable comparator).

The assessments and parameters discussed are suitable for comparisons of the effects of peptides or medicaments of the invention as compared to control, placebo or standard care treatment in animals or humans. Appropriate statistical tests may be used to analyse datasets generated from different treatments in order to investigate significance of results.

Preferably prevention, reduction or inhibition of scarring may be demonstrated with reference to more than one parameter. More preferably prevention, reduction or inhibition of scarring may be demonstrated with reference to both a clinical (i.e. observed on the subject) parameter and a photographic parameter. Even more preferably prevention, reduction or inhibition of scarring may be demonstrated with reference to a clinical parameter, a photographic parameter, and also a microscopic assessment parameter (for instance a histological parameter). Most preferably prevention, reduction or inhibition of scarring may be demonstrated with reference to a clinical VAS score, external lay panel VAS score and ranking (from photographic images) and microscopic VAS score of the reticular dermis.

The use of suitable methods and medicaments of the invention is able to bring about a rapid improvement in the cosmetic appearance of an injured area thus treated. Cosmetic considerations are important in a number of clinical contexts, particularly when wounds are formed at prominent body sites such as the face, neck and hands. Consequently the inhibition of scarring (which may preferably be in combination with accelerated wound healing) at such sites where it is desired to improve the cosmetic appearance of scar formed represents a preferred embodiment of the invention.

In addition to its cosmetic impact skin scarring is responsible for a number of deleterious effects afflicting those suffering from such scarring. For example, skin scarring may be associated with reduction of physical and mechanical function, particularly in the case of contractile scars (such as hypertrophic scars) and/or situations in which scars are formed across joints. In these cases the altered mechanical properties of scarred skin, as opposed to unscarred skin, and the effects of scar contraction may lead to dramatically restricted movement of a joint (articulation) so effected. Accordingly it is a preferred embodiment that suitable medicaments and methods of the invention be used to prevent, reduce or inhibit scarring of wounds covering joints of the body (preferably also accelerating healing of such wounds). In another preferred embodiment suitable medicaments and methods of the invention may be used to promote accelerated wound healing and/or prevent, reduce or inhibit scarring of wounds at increased risk of forming a contractile scar.

The extent of scar formation, and hence extent of cosmetic or other impairment that may be caused by the scar, may also be influenced by factors such as the tension of the site at which the wound is formed. For example, it is known that skin under relatively high tension (such as that extending over the chest, or associated with lines of tension) may be prone to formation of more severe scars than at other body sites. Thus in a preferred embodiment suitable medicaments and methods of the invention may be used to promote accelerated wound healing and/or prevent, reduce or inhibit scarring of wounds located at sites of high skin tension. There are many surgical procedures that may be used in scar revision to allow realignment of wounds and scars such that they are subject to reduced tension. Probably the best known of these is "Z-plasty" in which two V-shaped flaps of skin are transposed to allow rotation of a line of tension. Thus in a more preferred embodiment such medicaments and methods of the invention be used to promote accelerated wound healing and/or prevent, reduce or inhibit scarring of wounds during surgical revision of disfiguring scars.

Pathological scarring may have more pronounced deleterious effects than arise even as a result of relatively severe normal scarring. Common examples of pathological scars include hypertrophic scars and keloids. It is recognised that certain types of wound, or certain individuals may be predisposed to pathological scar formation. For instance individuals of Afro-Caribbean, Japanese or Mongoloid heritage, or those having a familial history of pathological scarring may be considered to be at increased risk of hypertrophic scar or keloid formation. Wounds of children, and particularly burns wounds of children, are also associated with increased hypertrophic scar formation. Accordingly it is a preferred embodiment of the invention that suitable medicaments and methods be used to promote accelerated wound healing and/or prevent, reduce or inhibit scarring of wounds in which there is an increased risk of pathological scar formation.

Although individuals already subject to pathological scarring suffer from a predisposition to further excessive scar formation it is often clinically necessary to surgically revise hypertrophic scars or keloids, with an attendant risk of consequential pathological scar formation. Thus it is a further preferred embodiment of the invention that suitable medicaments and methods be used to promote accelerated wound healing and/or prevent, reduce or inhibit scarring of wounds produced by surgical revision of pathological scars.

It is recognised that wounds resulting from burns injuries (which for the purposes of the present invention may be taken also to encompass scalding injuries involving hot liquids or gasses) may extend over great areas of an individual so afflicted. Accordingly, burns may give rise to scar formation covering a large proportion of a patient's body, thereby increasing the risk that the scar formed will cover areas of elevated cosmetic importance (such as the face, neck, arms or hands) or of mechanical importance (particularly the regions covering or surrounding joints). Burns injuries caused by hot liquids are frequently suffered by children (for example as a result of upsetting pans, kettles or the like) and, due to the relatively smaller body size of children, are particularly likely to cause extensive damage over a high proportion of the body area. It is a further preferred embodiment of the invention that suitable medicaments and methods be used to promote accelerated wound healing and/or prevent, reduce or inhibit scarring of wounds produced by burns injuries.

As noted above, wound healing in response to burns injuries is frequently associated with adverse scarring outcomes, such as the formation of hypertrophic scars. A further consequence of the relatively large size of burns injuries is that they are particularly susceptible to complications such as infection and desiccation that arise due to lack of a functional epithelial layer. In the light of the above it will be appreciated that suitable methods and medicaments of the invention may be used in the treatment of burn injuries to reduce the level of scarring that occurs as a result of the wound and/or accelerate the re-constitution of a functional epithelial barrier.

The inventors have found that methods and medicaments of the invention utilising monomers such as those comprising Sequence ID No. 3 are able to promote re-epithelialisation. Accordingly such methods and medicaments are particularly effective in the treatment of all injuries involving damage to an epithelial layer. Such injuries are exemplified by, but not limited to, injuries to the skin, in which the epidermis is damaged. It will however be appreciated that such methods and medicaments of the invention are also applicable to other types of wounds in which epithelia are damaged, such as injuries involving the respiratory epithelia, digestive epithelia or epithelia surrounding internal tissues or organs (such as the epithelia of the peritoneum).

The healing of wounds involving the peritoneum (the epithelial covering of the internal organs, and/or the interior of the body cavity) may frequently give rise to adhesions. Such adhesions are a common sequitur of surgery involving gynaecological or intestinal tissues. The inventors believe that the ability of the methods and medicaments of the invention (utilising suitable monomers such as those comprising Sequence ID No. 3) to accelerate the regeneration of the peritoneum while reducing scarring may reduce the incidence of inappropriate attachment of portions of the peritoneum to one another, and thereby reduce the occurrence of adhesions. Accordingly, the use of such methods and medicaments of the invention to prevent the formation of intestinal or gynaecological adhesions represents a preferred embodiment of the invention. Indeed the use of such methods or medicaments of the invention in the healing of any wounds involving the peritoneum is a preferred embodiment.

The methods or medicaments of the invention may be used prophylactically, for example at sites where no wound exists but where a wound that would otherwise give rise to a scar or chronic wound is to be formed. By way of example medicaments in accordance with the invention may be administered to sites that are to undergo wounding as a result of elective procedures (such as surgery), or to sites that are believed to be at elevated risk of wounding. It may be preferred that the medicaments of the invention are administered to the site around the time of wounding, or immediately prior to the forming of a wound (for example in the period up to six hours before wounding) or the medicaments may be administered at an earlier time before wounding (for example up to 48 hours before a wound is formed). The skilled person will appreciate that the most preferred times of administration prior to formation of a wound will be determined with reference to a number of factors, including the formulation and route of administration of the selected medicament, the dosage of the medicament to be administered, the size and nature of the wound to be formed, and the biological status of the patient (which may determined with reference to factors such as the patient's age, health, and predisposition to healing complications or adverse scarring). The prophylactic use of methods and medicaments in accordance with the invention is a preferred embodiment of the invention, and is particularly preferred in the promotion of accelerated wound healing and/or prevention, reduction or inhibition of scarring in the context of surgical wounds.

The methods and medicaments of the invention are also able to promote accelerated wound healing and/or inhibited scarring if administered after a wound has been formed. It is preferred that such administration should occur as early as possible after formation of the wound, but agents of the invention are able to promote accelerated wound healing and/or prevent, reduce or inhibit scarring at any time up until the healing process has been completed (i.e. even in the event that a wound has already partially healed the methods and medicaments of the invention may be used to promote accelerated wound healing and/or prevent, reduce or inhibit scarring in respect of the remaining un-healed portion). It will be appreciated that the "window" in which the methods and medicaments of the invention may be used to promote accelerated wound healing and/or prevent, reduce or inhibit scarring is dependent on the nature of the wound in question (including the degree of damage that has occurred, and the size of the wounded area). Thus in the case of a large wound the methods and medicaments of the invention may be administered relatively late in the healing response yet still be able to promote accelerated wound healing and/or prevent, reduce or inhibit scarring. The methods and medicaments of the invention may, for instance, preferably be administered within the first 24 hours after a wound is formed, but may still promote accelerated wound healing and/or prevent, reduce or inhibit scarring if administered up to ten, or more, days after wounding.

The methods and medicaments of the invention may be administered on one or more occasions as necessary in order to promote accelerated wound healing and/or prevent, reduce or inhibit scarring. For instance therapeutically effective amounts of the medicaments may be administered to a wound as often as required until the healing process has been completed. By way of example, the medicaments of the invention may be administered daily or twice daily to a wound for at least the first three days following the formation of the wound. The inventors have found that regimes involving two administrations of medicaments of the invention, the first prior to formation of a wound and the second after wounding, are particularly beneficial in reducing scar formation. Preferably such regimes may involve a first administration immediately prior to formation of a wound and a second administration 24 hours after wounding.

Most preferably the methods or medicaments of the invention may be administered both before and after formation of a wound. The inventors have found that administration of the medicaments of the invention immediately prior to the formation of a wound, followed by daily administration of such agents in the days following wounding, is particularly effective in promoting accelerated wound healing and/or prevent, reduce or inhibit scarring.

For the purposes of the present specification by "agent" or "agent of the invention" is meant biologically or therapeutically active monomeric TGF-β. Such agents may preferably be wild type monomeric TGF-βs, and more preferably may be monomeric TGF-βs capable of promoting accelerated wound healing and/or inhibiting scarring, of which a preferred example comprises the monomer set out in Sequence ID No. 3. It will be appreciated that all such agents may be incorporated in medicaments in accordance with the invention, and may be used in the methods or uses of the invention.

It will be appreciated that the amount of a medicament of the invention that should be applied to a wound depends on a number of factors such as the biological activity and bioavailability of the agent present in the medicament, which in turn depends, among other factors, on the nature of the agent and the mode of administration of the medicament. Other factors in determining a suitable therapeutic amount of a medicament may include:

A) The half-life of the agent in the subject being treated.
B) The specific condition to be treated (e.g. acute wounding or chronic wounds).

C) The age of the subject.

The frequency of administration will also be influenced by the above-mentioned factors and particularly the half-life of the chosen agent within the subject being treated.

Generally when medicaments in accordance with the invention are used to treat existing wounds the medicament should be administered as soon as the wound has occurred (or in the case of wounds that are not immediately apparent, such as those at internal body sites, as soon as the wound has been diagnosed). Therapy with methods or medicaments in accordance with the invention should continue until the healing process has been accelerated, and/or scarring prevented, reduced or inhibited, to a clinician's satisfaction.

Frequency of administration will depend upon the biological half-life of the agent used. Typically a cream or ointment containing an agent of the invention should be administered to a target tissue such that the concentration of the agent at a wound is maintained at a level suitable for having a therapeutic effect. This may require administration daily or even several times daily.

Medicaments of the invention, may be administered by any suitable route capable of achieving the desired effect of promoting wound healing and/or preventing, reducing or inhibiting scarring, but it is preferred that the medicaments be administered locally at a wound site.

The inventors have found that the promotion of accelerated wound healing and/or prevention, reduction or inhibition of scarring may be effected by the administration of an agent of the invention by injection at the wound site. For instance, in the case of dermal wounds, agents of the invention may be administered by means of intradermal injection. Thus a preferred medicament in accordance with the invention comprises an injectable solution of an agent of the invention (e.g. for injection around the margins of a site of epithelial damage or a site likely to be damaged). Suitable formulations for use in this embodiment of the invention are considered below.

Alternatively, or additionally, medicaments of the invention may also be administered in a topical form to promote accelerated wound healing and/or prevention, reduction or inhibition of scarring. Such administration may be effected as part of the initial and/or follow up care for the wounded area.

The inventors find that the promotion of accelerated wound healing and/or prevention, reduction or inhibition of scarring is particularly improved by topical application of an agent of the invention to a wound (or, in the case of prophylactic application, to a tissue or site where a wound is to be formed).

Compositions or medicaments containing agents of the invention may take a number of different forms depending, in particular on the manner in which they are to be used. Thus, for example, they may be in the form of a liquid, ointment, cream, gel, hydrogel, powder or aerosol. All of such compositions are suitable for topical application to a wound, which is a preferred means of administering agents of the invention to a subject (person or animal) in need of treatment.

The agents of the invention may be provided on a sterile dressing or patch, which may be used to cover a wound or other site of epithelial damage to be treated.

It will be appreciated that the vehicle of a composition comprising agents of the invention should be one that is well tolerated by the patient and allows release of the agent to the wound. Such a vehicle is preferably biodegradeable, bioresolveable, bioresorbable and/or non-inflammatory.

Medicaments and compositions comprising agents of the invention may be used in a number of ways. Thus, for example, a composition may be applied in and/or around a wound in order to promote accelerated wound healing and/or prevent, reduce or inhibit scarring. If the composition is to be applied to an "existing" wound, then the pharmaceutically acceptable vehicle will be one which is relatively "mild" i.e. a vehicle which is biocompatible, biodegradable, bioresolvable and non-inflammatory.

An agent of the invention, or a nucleic acid encoding such an agent (as considered further below), may be incorporated within a slow or delayed release device. Such devices may, for example, be placed on or inserted under the skin and the agent or nucleic acid may be released over days, weeks or even months. Such a device may be particularly useful for patients (such as those suffering from chronic wounds) that require long-term promotion of accelerated wound healing and/or prevention, reduction or inhibition of scarring. The devices may be particularly advantageous when used for the administration of an agent or nucleic acid that would normally require frequent administration (e.g. at least daily administration by other routes).

Daily doses of an agent of the invention may be given as a single administration (e.g. a daily application of a topical formulation or a daily injection). Alternatively, the agent of the invention may require administration twice or more times during a day. In a further alternative, a slow release device may be used to provide optimal doses of an agent of the invention to a patient without the need to administer repeated doses.

In one embodiment a pharmaceutical vehicle for administration of an agent of the invention may be a liquid and a suitable pharmaceutical composition would be in the form of a solution. In another embodiment, the pharmaceutically acceptable vehicle is a solid and a suitable composition is in the form of a powder or tablet. In a further embodiment the agent of the invention may be formulated as a part of a pharmaceutically acceptable transdermal patch.

A solid vehicle can include one or more substances that may also act as flavouring agents, lubricants, solubilizers, suspending agents, fillers, glidants, compression aids, binders or tablet-disintegrating agents; it can also be an encapsulating material. In powders, the vehicle is a finely divided solid that is in admixture with the finely divided agent of the invention. In tablets, the agent of the invention is mixed with a vehicle having the necessary compression properties in suitable proportions and compacted in the shape and size desired. The powders and tablets preferably contain up to 99% of the agent of the invention. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles may be used in preparing solutions, suspensions, emulsions, syrups, elixirs and pressurized compositions. The agent of the invention can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). It may generally be preferred that the medicaments or methods of the invention utilise formulations in which monomeric TGF-βs, such as TGF-β3, are provided in the absence of alcohols.

Such alcohol-free formulations may be particularly preferred for use at wound sites (or sites where wounds are to be formed) due to their relatively "mild" nature. For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

Liquid pharmaceutical compositions which are sterile solutions or suspensions can be utilized by for example, intramuscular, intrathecal, epidural, intraperitoneal, intradermal, intrastromal (cornea) or subcutaneous injection. Sterile solutions can also be administered intravenously. The agent of the invention may be prepared as a sterile solid composition that may be dissolved or suspended at the time of administration using sterile water, saline, or other appropriate sterile injectable medium. Vehicles are intended to include necessary and inert binders, suspending agents, lubricants and preservatives.

In the situation in which it is desired to administer an agent of the invention by means of oral ingestion, it will be appreciated that the chosen agent will preferably be an agent having an elevated degree of resistance to degradation. For example, the agent of the invention may be protected (for instance using the techniques described above) so that its rate of degradation in the digestive tract is reduced.

Compositions of agents of the invention are suitable to be used for promoting accelerated wound healing and/or inhibiting scarring in the cornea. Corneal wounds may result from trauma to the eye arising as a result of accidental injury (as considered above) or as a result of surgical operations (e.g. laser surgery on the cornea). In this case a preferred medicament of the invention may be in the form of an eye drop.

Agents of the invention may be used in a range of "internal" wounds (i.e. wounds occurring within the body, rather than on an external surface). Thus for example, medicaments in accordance with the invention may be formulated for inhalation for use in wounds arising in the lungs or other respiratory epithelia.

Known procedures, such as those conventionally employed by the pharmaceutical industry (e.g. in vivo experimentation, clinical trials etc), may be used to establish specific formulations of compositions comprising agents of the invention and precise therapeutic regimes for administration of such compositions (such as daily doses of the active agent and the frequency of administration).

A suitable daily dose of an agent in accordance with the invention able to promote accelerated wound healing and/or prevention, reduction or inhibition of scarring depends upon a range of factors including (but not limited to) the nature of the tissue wounded, area and/or depth of the wound to be treated, the severity of the wound, and the presence or absence of factors predisposing to pathological scar or chronic wound formation.

By way of example, the amount of an active agent that may be administered to a wound or site of epithelial damage in a single incidence of treatment may preferably be in the region of 50-200 ng/linear cm of wound or $cm^2$ epithelial damage (if administered by injection), or 100-300 ng/linear cm of wound or $cm^2$ of epithelial damage (if administered topically).

By way of further example, the preferred amount of an active agent to be administered daily to a wound or site of epithelial damage may be in the region of 50 ng/linear cm of wound or $cm^2$ epithelial damage (if administered by injection), or 100 ng/linear cm of wound or $cm^2$ epithelial damage (if administered topically).

By way of example, the total amount of an active agent that may be administered by local injection to a wound or site of epithelial damage may be preferably be in the region of 50 ng/100 µL per linear centimeter of wound or $cm^2$ epithelial damage, given once a day for up to three days, thereby providing a total dose of 150 ng/linear centimeter of wound or $cm^2$ epithelial damage.

In the case of topical application to acute wounds or sites of epithelial damage, a suitable amount of an active agent may preferably be in the region of 100 ng/linear of wound or $cm^2$ or epithelial damage, given once a day for up to 3 days, thereby providing a total dose of 300 ng/linear cm of wound or $cm^2$ of epithelial damage.

Without detracting from the above, the amount of an agent in accordance with the invention required for the treatment of wounds or other sites of epithelial damage will typically be within the range of 1 pg to 1 mg of the agent administered per linear centimeter of wound or epithelial damage per 24 hours, although this figure may be modified upwards or downwards in response to the factors outlined above. The agent may preferably be provided in the form of a 1 pg/100 µL-1 mg/100 µL solution of the agent, and 100 µL of such a solution administered per linear centimeter of wound or epithelial damage over a 24 hour period.

The agent may more preferably be administered as a 10 pg/100 µL-100 µg/100 µL solution with 100 µL of such a solution administered per linear centimeter of wound or epithelial damage over a 24 hour period.

Most preferably the agent may be administered as a 1 ng/100 µL-1000 ng/100 µL solution with 100 µL of such a solution administered per linear centimeter of wound or epithelial damage over a 24 hour period.

Generally, compositions comprising agents of the invention should be formulated such that when administered to a wound a concentration of the agent of between 0.79 pM and 0.79 mM per linear centimeter of wound or epithelial damage is achieved. Preferably the agent may be provided at concentrations of between 7.9 pM and 0.079 mM per linear centimeter.

An agent of the invention (such as the peptide of Sequence ID No. 3) may be administered at a concentration of between 0.79 pM and 0.79 mM. Preferably an agent of the invention may be administered at a concentration of between 7.9 pM and 0.079 mM. Most preferably an agent of the invention may be administered at a concentration of between 0.79 nM and 0.79 µM.

Purely by way of example an injectable solution containing between 10 pg/100 µL and 100 µg/100 µL of an agent of the invention (such as the peptide of Sequence ID No. 3) is suitable for application to promote accelerated dermal wound healing and/or inhibition of scarring when administered as an intradermal injection and dosed with 100 µL per linear cm of wound margin.

In the case of a monomeric peptide of Sequence ID No. 3, preferred dosages for administration to a wound may be in the region of 1 ng/100 µL-1000 ng/100 µL, and 100 µL of such a solution administered per linear cm of wound margin.

Agents of the invention may be used to promote accelerated wound healing and/or prevent, reduce or inhibit scarring as a monotherapy (e.g. through use of medicaments of the invention alone). Alternatively the methods or medicaments of the invention may be used in combination with other compounds or treatments for the promotion of wound healing or scar inhibition. Suitable treatments that may be used as parts of such combination therapies will be well known to those skilled in the art.

The inventors have found that medicaments in accordance with the present invention, and particularly those comprising peptides of Sequence ID No. 3 may be advantageously formulated in the presence of a sugar. This sugar may be a reducing or non-reducing sugar and/or a phosphate or phosphonate derivative thereof. Examples of such sugars may be selected from, but are not limited to, the group comprising maltose, mannose, trehalose, arabinose, mannitol, sucrose, fructose, dextrose and glucose. Preferred sugars may be selected from the group consisting of maltose and trehalose. Medicaments of the invention, and particularly those in accordance with this embodiment of the invention, may preferably have a pH of between 5 and 7.

It will be appreciated that monomeric TGF-β peptides may represent favourable agents to be administered by techniques involving cellular expression of nucleic acid sequences encoding such molecules. Such methods of cellular expression are particularly suitable for medical use in which the therapeutic effects of the peptides are required over a prolonged period, for example in contexts where it is desirable to augment over a period of time an otherwise defective wound healing response. It is particularly preferred that TGF-β monomers to be administered via cellular expression comprise peptides defined by Sequence ID No. 3.

Many known methods of administering peptide agents of the invention to tissues such as wounds have the disadvantage that it can be difficult to achieve sustained levels of the agent of the invention at the treatment site over the course of even a few days because the peptide agents may have short half-lives in vivo. The half-lives of the agents may be short for a number of reasons which include:
 (i) Degradation by proteases and the like.
 (ii) Clearance by binding proteins.
 (iii) Binding and inhibition of agent activity by extracellular matrix molecules.

Furthermore, agents used to promote accelerated wound healing and/or prevention, reduction or inhibition of scarring need to be administered in a suitable vehicle and are often provided as a composition comprising the agent and the vehicle. As discussed, such vehicles are preferably non-inflammatory, biocompatible, bioresorbable and must not degrade or inactivate the agent (in storage or in use). However, it can often be difficult to provide a satisfactory vehicle for delivering agents to a tissue with a wound to be treated.

A convenient way in which these problems can be obviated or mitigated is to provide a therapeutically effective amount of an agent of the invention at an area to be treated by means of gene therapy.

Due to the degeneracy of the genetic code, it is clear that nucleic acid sequences encoding agents suitable for use in accordance with the invention may be varied or changed without substantially affecting the sequence of the product encoded thereby, to provide a functional variant thereof. The sequences of possible nucleic acids that may be used to encode peptides defined by Sequence ID Nos. 1 to 3 will be readily apparent to the skilled person, and suitable examples are provided as Sequence ID Nos. 4 to 7 respectively.

Gene therapy delivery systems are highly suitable for achieving sustained levels of an agent of the invention at a wound over a longer period of time than is possible for most conventional delivery systems. Agents of the invention suitable for promoting accelerated wound healing and/or inhibited scarring may be continuously expressed from cells at a wound site that have been transformed with the DNA molecule disclosed in the ninth aspect of the invention. Therefore, even if the agent of the invention has a very short half-life in vivo, therapeutically effective amounts of the agent may be continuously expressed from the treated tissue.

Furthermore, gene therapy delivery systems may be used to provide the DNA molecule (and thereby the agent of the invention) without the need to use conventional pharmaceutical vehicles such as those required in ointments or creams that are contacted with the wound.

A suitable gene therapy delivery system is preferably such that the DNA molecule is capable of being expressed (when the delivery system is administered to a patient) to produce a peptide defined by the group comprising Sequence ID Nos. 1 to 3. The DNA molecule may be contained within a suitable vector to form a recombinant vector. The vector may for example be a plasmid, cosmid or phage. Such recombinant vectors are highly useful in gene therapy delivery systems of the invention for transforming cells with suitable DNA molecules.

Recombinant vectors may also include other functional elements. For instance, recombinant vectors may be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one that becomes incorporated in the DNA of cells of the subject being treated. Undifferentiated cells may be stably transformed leading to the production of genetically modified daughter cells. When this is the case, regulation of expression in the subject may be required e.g. with specific transcription factors, gene activators or more preferably with inducible promoters which transcribe the gene in response to a signal specifically found at a wound. Alternatively, the delivery system may be designed to favour unstable or transient transformation of differentiated cells in the subject being treated. In this instance, regulation of expression may be less important because expression of the DNA molecule will stop when the transformed cells die or stop expressing the protein (ideally when the promotion of accelerated wound healing with reduced scarring has been effected).

The delivery system may provide the DNA molecule to a subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to a wound topically or by injection.

Cellular expression of the agent of the invention may be by cells at the edge of the undamaged area surrounding the wound, or may alternatively be by cells therapeutically introduced into the wound (for example cultured endogenous or exogenous cells involved in the wound healing response).

It will be appreciated that cells that are to be introduced therapeutically to promote accelerated wound healing and/or prevention, reduction or inhibition of scarring may be manipulated ex vivo such that they express increased levels of an agent of the invention, and then introduced into the wounded area. Such cells may preferably be cells cultured ex vivo for use in the preparation or manufacture of artificial skin or skin substitutes to be used in the promotion of wound healing. The cells may more preferably be autologous cells, although it will be appreciated that any suitable cells may be used.

Accordingly, in a seventeenth aspect of the invention, there is provided a medicament comprising cells induced to express an agent of the present invention. Such cells may preferably express a monomeric TGF-β3.

The induction of cellular expression of an agent of the invention may be effected by means of the incorporation in the cells of nucleic acids causing the expression of agents suitable for use in accordance with the invention.

The invention will now be further described by way of example with reference to the following experimental protocols and studies, and the accompanying Figures in which:

FIG. 1 illustrates the results of comparison of monomeric and dimeric forms of TGF-β3 by SDS-PAGE under both reduced and non-reduced conditions;

FIG. 2 sets out the template used for positioning of incisional wounds on experimental rats;

FIG. 3 summarises treatments administered to wound sites of experimental animals;

FIG. 4 shows results of assessment, three days after wounding, of the appearance of experimental wounds treated with monomeric or dimeric TGF-β3;

FIG. 5 summarises treatments administered to wound sites of experimental animals;

FIG. 6 shows results of assessment, 70 days after wounding, of the appearance of experimental scars treated with monomeric or dimeric TGF-β3;

FIG. 7 shows representative macroscopic images showing the appearance of experimental scars 70 days after wounding;

Figure 9:
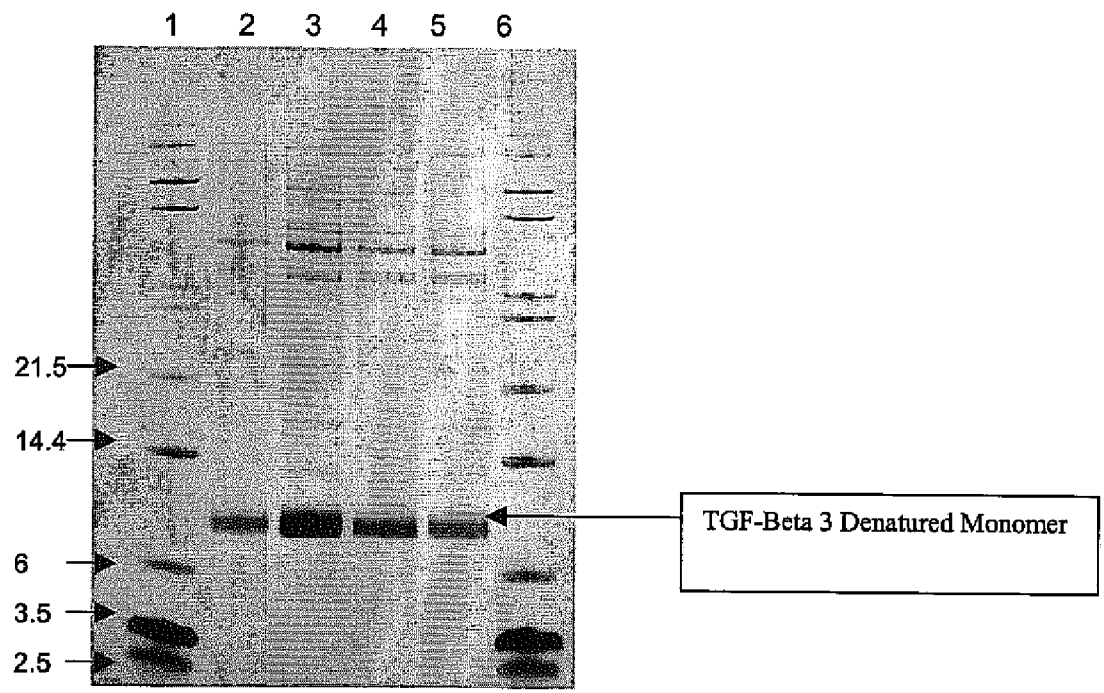
Figure 10:
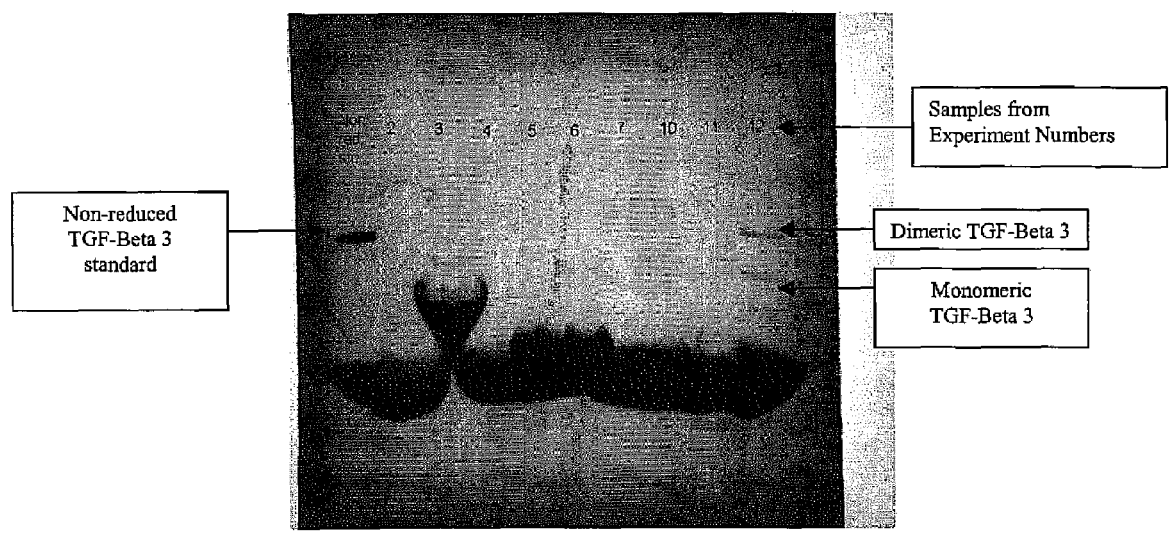
Figure 11:
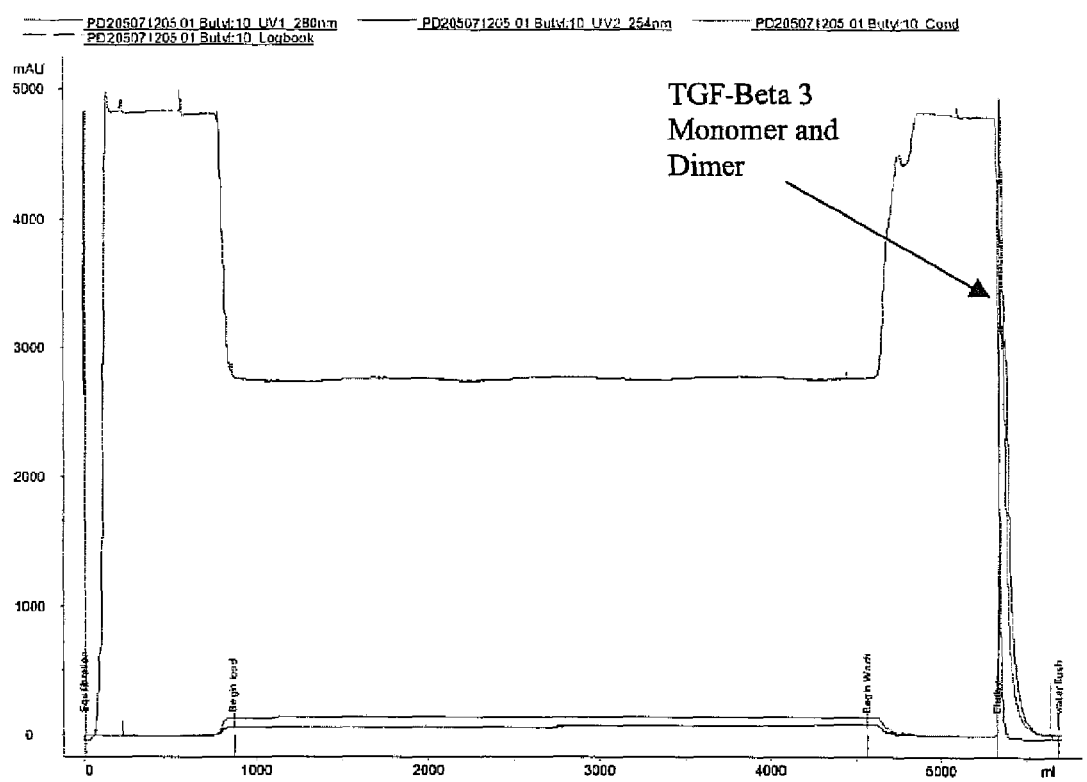

FIG. 8 representative microscopic images showing the structure of experimental scars 70 days after wounding FIG. 9 illustrates production of TGF-β3 monomers by successfully transformed host cells;

FIG. 10 illustrates generation of dimeric and monomeric TGF-β3 under experimental protein refolding conditions; and FIG. 11 illustrates isolation of TGF-β3 proteins by ultrafiltration/hydrophobic interaction chromatography.

Information regarding amino acid or nucleic acid sequences of importance is provided in the section "Sequence Information" (including the amino acid sequences of the active fragments of human TGF-β isoforms suitable for use in accordance with the invention, as well as the sequences of DNA molecules encoding full-length peptides of the TGF-β isoforms, and DNA encoding the active fragment of wild type TGF-β3; and the DNA sequences of primers used in the generation of cDNA encoding human TGF-β isoforms suitable for use in accordance with the invention).

PROTOCOLS AND EXAMPLES

1. Methodologies for the Production, Refolding, and Purification of TGF-β Monomeric Proteins 1.1 Nucleotide Sequences DNA sequences encoding full-length TGF-β proteins are shown as Sequence ID Nos. 4 to 6. Full-length TGF-β proteins consist of a signal peptide (shown in italics), pro-peptide (shown in bold) as well as the active fragment (shown in normal text). The nucleotide sequence coding for the wild type TGF-β3 active fragments is shown in Sequence ID No. 7.

1.2 cDNA Generation

Total RNA from a human incisional wound (taken day 5 post-wounding) was treated with 'DNA-Free' (Ambion) to remove any contaminating DNA. Using total RNA as a template, cDNA for each of the three mammalian TGF-β isoforms i.e., TGF-β1, TGF-β2 and TGF-β3 was generated by Reverse Transcriptase-Polymerase Chain Reaction (RT-PCR). The RT-PCR master mix was prepared from Brilliant® QRT-PCR Core Reagent Kit, 1-Step (Stratagene). One microgram of RNA was added to 50 µL of a solution containing: One-step QRT-PCR buffer, 0.2 mM dNTPs, 3.5 mM $MgCl_2$, 1 µL StrataScript reverse transcriptase, TaqPolymerse 2.5 units, 0.4 µM Sense primer (FIG. 1), 0.4 µM Anti-Sense primer (as shown in Sequence Information). The reaction was placed in a thermal cycler (Hybrid PCR Expresses) and run under the following conditions: 30 min at 45° C., 10 min at 95° C., then 40 cycles of 95° C. for 30 sec, 65° C. for 1 min and 72° C. for 1 min. Final step of 72° C. for 10 min. PCR samples were run on 2% (w/v) agarose gels to verify band size and purified using Wizard PCR Prep Kit (Promega).

1.3 Construction of Plasmid

The pET-3d vector used is derived from pBR322 vector and contains a T7 promoter under LacUV5 control and an Ampicillin resistant marker gene.

The three TGF-β isoform cDNA fragments (generated in Section 1.2) were sub-cloned into pET-3d vectors at the Nco I and Bam HI sites (5'-3' respectively). The resulting ligations were then transformed into XL10 Gold cells (Stratagene) and colony PCR analysis was performed to locate clones containing an insert. The final clones were grown up and their plasmid DNA extracted into water using Qiaprep®Spin Miniprep Kit (Qiagen). The plasmids were sequenced and verified using T7 promoter primer (5'-TAA TAC GAC TCA CTA TAG GG-3') and T7 terminator primer (5'-GCT AGT TAT TGC TCA GCG G-3').

1.4 Transformation and Cloning

10 µL (50 ng per µl) of plasmid DNA encoding for each of the TGF-β isoforms (from Section 1.3) was added to 1 mL of cold (4° C.) competent E. coli BL21 (DE3) pLysS Singles™ cells (Novagen). After 20 min the cells were heat shocked by incubation for 30 sec at 42° C. in a water bath. 100 µL of Psi medium was added to the cell/plasmid mixture and shaken at 37° C. for 90 min. 50 µl and 100 µl aliquots were plated onto LB agar plates containing 100 µg/mL Ampicillin (Sigma) and incubated for 18 hours at 37° C. Single colonies were cultivated and frozen cell stocks generated and stored at −80° C. Plasmid DNA was analysed from cells stocks to verify correct transformation.

1.5 Expression

Ampoules of frozen E. coli cells that transformed with each of the TGF-β isoforms (from Section 1.4) were recovered and inoculated into baffled Erlenmeyer flasks, containing 100 mL of LB media and 100 µg/mL of Ampicillin. The flasks was incubated with shaking, overnight at 37° C. 5 mL of this overnight culture were added to 2-liter Erlenmeyer flasks (500 mL of LB media/amp) and incubated with shaking at 37° C. 2 mL Broth samples were taken hourly to track growth and TGF-β isoform expression (post-induction). Growth was determined by measuring absorbance on a spectrophometer, at a wavelength of 600 nm. When the absorbance measured 0.6 Abs the cells were induced to express the TGF-β isoforms by the addition of Isopropyl β-D-Thiogalctopyranoside (IPTG, Sigma) to a final concentration of 1 mM. The cultures were incubated for an additional 4 hours. The 0.5 mL of broth samples were pelleted by centrifugation (10 min 10,000 rpm in a Sorvall Biofuge) and the supernatant discarded. The pellet was re-suspended in 50 μL of Sodium Dodecyl Sulfate (SDS)-polyacrylamide gel-electrophoresis (PAGE) sample buffer and heated for 10 minutes in a water bath at 95° C. 10 μL samples were loaded onto SDS-PAGE. SDS-PAGE and Coomassie Blue staining was performed (as described in A. T Andrews, 1986) using a Hoefer® Mighty Small SE 245 Dual Gel Caster (Amersham). The gels were 1 mm thick and contained 15% (v/v) polyacrylamide gel.

1.6 Cell Harvesting and Isolation of Inclusion Bodies

Cells from Section 1.5 were pelleted by centrifuging at 5000 g for 10 min at 4° C. in a Hettich Rotina 46R centrifuge with a 4315 Rotor. Cell disruption and recovery of each of the insoluble (inclusion bodies) TGF-β isoforms were performed at 4° C. The cells were suspended in 50 mL of 100 mM Tris/HCl (Sigma), 10 mM EDTA (Sigma) pH 8.3 and were disrupted by sonication using a Sanjo Soniprep 150. 0.2% (w/w) Triton X-100 (Sigma) was added and the suspension and stirred for one hour. The suspension was centrifuged at 12,000 g for 40 min. The pellets were re-suspended in 50 mL of 100 mM Tris/HCl, 10 mM EDTA pH 8.3 at room temperature before being centrifuged for 40 min at 15,000 g.

1.7 Solubilisation of Inclusion Bodies

The pellets from Section 1.6 were re-suspended in 40 mL of 8M Urea 1% (w/w) DL-Dithiothreitol (DTT) and disrupted in a Heidolph Diax 900 homogeniser. The suspension was covered and left stirring for 1 hour to solubilise the inclusion bodies and reduce TGF-β isoforms to their denatured monomeric form. The suspensions were then centrifuged at 12,000 g for 30 min at 4° C. The supernatants were dialysed to exchange buffer from 8M Urea (ICN Biomedical) to 10% (v/v) acetic acid. The *E. coli* proteins that were soluble in the 8M urea precipitate out of solution when the buffer is exchanged to 10% (v/v) acetic acid. 1% (w/v) DTT (Sigma) was added to the suspensions, covered and left stirring for 30 min to reduce any disulfide bonds that may have formed between TGF-β monomers during the buffer exchange. The suspensions were centrifuged to separate the soluble and non-soluble proteins. Samples were taken from Urea solubilisation and buffer exchange steps (acetic acid soluble and non-soluble material), and then analysed using SDS-PAGE.

1.8 Ultrafiltration

The 10% (v/v) acetic acid material from Section 1.7 underwent ultrafiltration with a 10 kDa membrane on a Vivoflow50 (Vivascience). The purpose of this was to reduce the volume of 10% (v/v) acetic acid suspension to 3 mL and to remove low molecular weight proteins (<10 kDa).

1.9 Refolding and Purification

The solubilised TGF-β1, 2 and 3 proteins were first concentrated by ultrafiltration and then run through a size-exclusion chromatography (SEC) column. The fractions from SEC containing TGF-β protein were then pooled and lyophilised. The lyophilised, monomeric, TGF-β1, 2 and 3 were solubilised in 8M urea containing 10 mM DTT until a final concentration of 10 mg/mL was achieved. The TGF-β1, 2 and 3 protein solutions were added drop wise, while stirring to re-folding solution (1M 3-(-Pyridino)-1-propane Sulfonate (NDSB-201), 20% (v/v) Dimethyl Sulfoxide (DMSO, Sigma), 2% (w/v) 3-(3-cholamidopropyl) dimethylammonio-1-propanesulfonate (CHAPS), 1M NaCl (Sigma), 1% (w/v) reduced Glutathione (GSH, Sigma), 0.05M Trizma® Base (Sigma) pH 9.3) until final concentrations of 0.2 mg/mL TGF-β1, 2 and 3 proteins were achieved. It is important the pH is kept within a range of 9.2-9.4 using concentrated NaOH/HCl. The solution was covered with Parafilm, which was punctured to allow oxidation of the monomeric proteins and left stirring at 8° C. After 144 hours the solution was centrifuged at 15,000 g for 40 minutes to remove the precipitate formed and the pH was adjusted to pH 3.5 with glacial acetic acid.

1.10 Purification of Refolded Monomeric Proteins

The resultant refolded TGF-β material was then further purified using standard chromatographic techniques followed by concentration of the relevant fractions (i.e. containing monomeric TGF-β proteins) by ultrafiltration prior to characterisation.

2. In-Vitro and In-Vivo Methodology for the Characterisation and Evaluation of Biological Activity of Monomeric TGF-β Proteins The TGF-β monomeric proteins were characterised and evaluated for biological activity via a number of methods including: SDS-PAGE; amino acid sequence analysis (by LCMS); in-vivo biological activity assay (using rat models of cutaneous wound healing and scarring described below).

2.1 In-Vitro Characterisation of TGF-β3 Monomers

2.1.1 Non-Reducing and Reducing SDS-PAGE Analysis of Purified Monomeric TGF-β3

2.1.1.1 Method

Purified wild type TGF-β3 monomers were assessed by SDS-PAGE to determine purity and molecular mass. 3 μg of purified TGF-β3 monomers (reduced and non-reduced samples), 3 μg dimeric TGF-β3 positive control (reduced and non-reduced) and 10 μL Invitrogen Mark 12 molecular weight standards were loaded onto a polyacrylamide gel (10%-20% (v/v) gradient of Acrylamide). Once the electrophoresis was complete the gel was stained with Coomassie Blue.

2.1.1.2 Results

The results of non-reducing and reducing SDS-PAGE analysis are shown in FIG. 1, and illustrate that dimeric TGF-β3 ran to expected positions on the gel (~13 kDa for reduced as monomers and 25 kDa for the non-reduced samples). The monomeric TGF-β ran to the expected ~13 kDa (12.5 kDa theoretical) position on the gel for reduced and non-reduced samples. No additional protein bands were detected by Coomassie Blue Staining, which has a sensitivity of approximately 1 μg of protein.

2.1.2 Amino Acid Sequence Analysis

2.1.2.1 Method 50 micro liters of purified monomeric TGF-β3 was vacuum dried and then re-suspended in 20 μl of a solution containing 50 mM NH$_4$HCO$_3$ and 10% (v/v) Acetonitrile. 20 μg of sequencing grade Trypsin (Promega) was re-suspended in 10 μl of kit supplied re-suspension buffer (Promega) to give a Trypsin concentration of 2 μg/μl. This was then diluted into 50 mM NH$_4$HCO$_3$ and 10% (v/v) Acetonitrile to give a final trypsin concentration of 0.2 μg/μl. The digestion was performed overnight by the addition of trypsin in a 1:20 (w/w) ratio of monomeric TGF-β3. The digestion was quenched by the addition of formic acid (Fluka) to a final concentration of 0.1% (v/v). The samples were then diluted to 1 pmole/μl the peptides were then analysed by a process of nano-flow RP-LCMS (Ultimate system, Dionex online to a Q-ToF2, Micromass). The chromatography was performed on a 75 μm C18 column (LC packings) utilising a 45 min gradient from 5% acetonitrile to 55% acetonitrile (Romil). The MS analysis took the form of data dependent analysis where the instrument measured the m/z of peptide ions eluting from the LC and selecting appropriate ions for MSMS analysis where collisionally induced decomposition was employed to fragment peptide ions to render sequence information.

2.1.2.2 Results

The amino acid sequence analysis confirmed that the TGF-β3 'wild-type' monomer had the expected amino acid sequence (corresponding to Sequence ID No. 3).

2.2 In-Vivo Evaluation of the Biological Activity of TGF-β3 Monomers

Data in the literature has demonstrated that dimeric TGF-βs including TGF-β3, accelerate cutaneous healing and reduce scarring following wounding or injury (Shah, M et al 1995). The following Example investigated the biological effects of monomeric TGF-β3 on incisional wound healing (3 days post-wounding) and scarring (70 days post-wounding) in adult, male rats.

2.2.1 The Effect of Monomeric 'Wild-type' and Mutated TGF-β3 Proteins on Wound Healing (Day 3 Incisional Wounding)

2.2.1.1 Method

Male rats (Sprague Dawley) were anaesthetized with Halothane and their backs shaved. Wounding positions were marked using a standard proprietary template with skin marking ink as shown in FIG. 2. Samples were diluted in sterile vehicle buffer containing 0.25M Maltose (Sigma), 0.002% (v/v) acetic acid and 0.33% (v/v) Isopropyl Alcohol to concentrations outlined in the Table of FIG. 3. All samples were filter sterilised and endotoxin free. Four rats were used for each treatment group. 100 μL of sample from each treatment group (FIG. 3) was injected intra-dermally into marked wound positions A and B (except rats receiving no treatment—"naïve"). At wound positions A and B full thickness 1 cm long incisions were made with a No. 11 scalpel blade. All animals were caged separately. After 24 hours the animals received a second dose of sample. After 3 days wounds were photographed and analysed using a macroscopic Visual Analogue Scoring system (modified from Beausang, E et al. 1998). Statistical analysis of the data was performed using Mann Whitney U/Student T tests. A value of p<0.05 was considered significant.

2.2.1.2 Results

Incisional wounds were examined after 3 days using macroscopic VAS system (see FIG. 4). On this ten-point scale a score of 0 represents a well-healed wound and a score of 10 represents a very poorly healed wound. Data shows that:

Treatment with 50 ng/100 μL or 100 ng/100 μL of 'wild-type' monomeric TGF-β3 decreases the VAS score (i.e., improves the macroscopic appearance of wounds) compared to both no treatment (naïve control) and placebo treatment. Treatment with the 100 ng/100 μL dose significantly improved (p<0.01) the appearance of wounds compared to no treatment (naïve control). It is surprising to note that monomeric Wild-type TGF-β showed greater effectiveness than did the dimeric form.

2.2.2 The Effect of Monomeric 'Wild-type' TGF-β3 Proteins on Scarring (Day 70 Incisional Wounding)

2.2.2.1 Method

Male rats (Sprague Dawley) were anaesthetized with Halothane and their backs shaved. Wounding positions were marked using a standardised template with skin marking ink as shown in FIG. 5. Samples were diluted in sterile vehicle buffer containing 0.25M Maltose (Sigma), 0.002% (v/v) acetic acid and 0.33% (v/v) Isopropyl Alcohol to concentrations outlined in the Table of FIG. 5. All samples were filter sterilised and endotoxin free. Four rats were used for each treatment group. 100 μL of sample from each treatment group (FIG. 5) was injected intra-dermally into marked wound positions A and B (except rats receiving no treatment—"naïve"). At wound positions A and B full thickness 1 cm long incisions were made with a No. 11 scalpel blade. All animals were caged separately. After 24 hours the animals received a second dose of sample. After 70 days scars were photographed and analysed using a macroscopic Visual Analogue Scoring system (modified from Beausang, E et al. 1998). Representative examples of the macroscopic appearance of scars produced as described above are shown in FIG. 7.

After macroscopic analysis, the wounds were excised and placed into 10% buffered saline before being processed for histological assessment into wax blocks. The wax blocks were cut into 5 μm serial sections and placed on slides. The slides were stained with Massons Trichrome and analysed. Statistical analysis of the data was performed using Mann Whitney U/Student T tests. A value of p<0.05 was considered significant. Representative examples of the microscopic appearance of scars produced as described above are shown in FIG. 8.

2.2.2.2 Assessment of Day 70 Incisional wounds using Macroscopic VAS

Incisional wounds were examined after 70 days using a macroscopic VAS system. A score of 10 indicates a bad scar and a score of 0 is normal skin. The results of VAS analysis of the day 70 wounds are summarised in FIG. 6. This shows that:

Monomeric 'Wild-type' TGF-β3 (at 50 ng/100 μL and 100 ng/100 μL doses) reduced scarring compared to the placebo treated and naïve wounds. For the 100 ng/100 μL dose this reduction is statistically significant compared to placebo treated wounds (p<0.01).

Dimeric TGF-β3 at 50 ng/100 μL reduced scarring compared to the placebo treated and naïve wounds. This reduction is statistically significant compared to placebo treated wounds (p<0.01).

3. Development of Preferred Conditions for the Production of Biologically Active Monomers The inventors investigated whether or not improved methods of generating correctly folded, biologically active TGF-β monomers could be established. The following example is illustrative of the application of the methods of the invention to the re-folding monomeric of TGF-β3.

A study was set up to screen re-fold reagents (see 3.12). Then methods of purifying the correctly refolded monomers were investigated (3.13).

These studies lead the inventors to realise that improved methods of generating biologically correctly folded TGF-βmonomers may be established by following a method comprising adding solubilised, unfolded monomeric growth factor to a solution containing:

(i) 2-(cylcohexylamino)-ethanesulfonic acid (CHES) or a functional analogue thereof; and (ii) a low molecular weight sulfhydryl/disulfide redox system; and incubating the growth factor in the solution until dimeric biologically active growth factor is formed.

Experimental

3.1 cDNA Generation

Total RNA from a human incisional wound (taken day 5 post-wounding) was treated with DNA-Free (Ambion) to remove any contaminating DNA. Using total RNA as a template, TGF-β3 cDNA was generated by Reverse Transciptase-Polymerase Chain Reaction (RT-PCR). The RT-PCR master mix was prepared from Brilliant® QRT-PCR Core Reagent Kit, 1-Step (Stratagene). One microgram of RNA was added to 50 µL of a solution containing: One-step QRT-PCR buffer, 0.2 mM dNTPs, 3.5 mM MgCl$_2$, 1 µL StrataScript reverse transcriptase, Taq Polymerase 2.5 units, 0.4 µM Sense primer (5' GAT ATA CCA TGG CTT TGG ACA CCA ATT ACT ACT GC 3'), 0.4 µM Sense primer (5'-CAG CCG GAT CCG GTC GAC TCA GCT ACA TTT ACA AGA C 3'). The reaction was placed in a thermal cycler (Hybrid PCR Express) and run under the following conditions: 30 min at 45° C., 10 min at 95° C., then 40 cycles of 95° C. for 30 sec, 65° C. for 1 min and 72° C. for 1 min. Final step of 72° C. for 10 min. PCR samples were run on 2% (w/w) agarose gel to verify band size and purified using Wizard PCR Prep Kit (Promega).

3.2 Vector Cloning and Host Cell Transformation

The pET-24d vector is derived from pBR322 vector and contains a T7 promoter under LacUV5 control and a kanamycin resistant marker gene.

The TGF-β3 cDNA fragments (generated in Section 1.1) were digested with 0.75 µL of Ncol (New England Biolabs) and 0.75 µL of BamH1 (New England Biolabs) with 1× BamH1 Buffer (New England Biolabs) in a 15 µL reaction (Nuclease Free Water, Novagen) at 37° C. for 4 hours. One microliter of pET-24d plasmid (Novagen) was digested in the same manner. The digested cDNA and the large plasmid fragment were agarose gel purified and recovered using the SpinPrep Gel DNA extraction kit (Novagen).

The purified cDNA and plasmid fragments were ligated using T4 ligase kit (Novagen). The ligated cDNA/plasmid was transformed into HMS174 (DE3) (Novagen HMS174 (DE3) transformation kit). The transformants were selected by plating on Luria broth (LB) agar plates containing 50 µg/mL kanamycin (Invitrogen). Three clones were selected for restriction digest and/or expression.

3.3 Clone Screening for Product Expression

Clones were grown in shake flask cultures of half strength 'Terrific Broth' (6 g/L phytone peptone (Becton Dickinson), 12 g/L yeast extract (Becton Dickinson), 2 g/L glycerol (JT Baker), 1.16 g/L potassium phosphate monobasic (JT Baker), 6.25 g/L potassium phosphate dibasic (JT Baker), QS to 1 Liter with distilled water) and induced in exponential phase at OD$_{600}$ between 0.65 and 0.85 with 1 mM isopropyl beta-D-thiogalactopyranoside (IPTG). Post-induction samples were taken 3 hours after the addition of IPTG and analysed by sodium dodecylsulfate polyacrylamide gel electrophoresis (SDS-PAGE) for product induction and expression. Clones 1-4 pre/post induction sample aliquots and Mark 12 molecular weight standards (Invitogen—molecular weight range 2.5-200 kDa) were run on NuPAGE® Novex 12% Bis-Tris Gel, 1.0 mm (Invitrogen) for approximately 40-50 minutes at 120 milliAmps and 200 Volts and then stained with Coomassie Blue. A protein whose size is between 6 and 14.4 kDa (i.e., TGF-β3 monomer) is clearly induced in each of these cultures (see FIG. 9) with Clone 2 expressing the greatest amount of TGF-µ3 protein.

3.4 Frozen Cell Stock

Clones 1-4 were grown in shake flasks in half strength Terrific Broth to an OD$_{600}$ of approximately 1. and stored as glycerol stocks by the addition of glycerol to 20% (v/v). 1.2 mL of broth was aliquoted into 12×2 mL cryovials (which contained 0.3 mL of glycerol) and then stored at −70° C.

3.5 Sequence Confirmation of TGF-Beta 3 Gene

Samples of the cultures used for frozen cell stocks were taken before the addition of glycerol and used for plasmid isolation using a Qiagen MiniPrep Kit. The isolated plasmid was sequenced and verified using a T7 promoter primer (5'-TAA TAC GAC TCA CTA TAG GG-3') and a T7 terminator primer (5'-GCT AGT TAT TGC TCA GCG G-3').

3.6 Seed Culture

As Clone 2 expressed the highest amount of TGF-Beta 3 protein an ampoule of frozen stock (from Section 3.4) was recovered and inoculated into a 2 Liter baffled Erlenmeyer flask, containing 500 mL of HySoy medium (12 g/L Hy-Soy (Quest International), 24 g/L yeast extract (Becton Dickinson), 10 g/L NaCl (Sigma) and 10 g/L glycerol (Sigma) and 50 µg/mL of kanamycin. The flask was incubated with shaking at 37° C. and 200 rpm and sampled periodically to measure OD$_{550}$. When the OD of the culture reached 3.21 U/mL (after 7 hours) the cell broth was used to seed a 150 L fermented (100 L working volume).

3.7 Fermentation

Nine hundred milliliters of cell broth (from Section 3.6) was used to inoculate a 150 L fermentor (WHE) containing 90 L of Batch Culture Media (0.6 g/L K$_2$HPO$_4$, 0.4 g/L KH$_2$HPO$_4$, 1.25 g/L NH$_4$SO$_4$, 12 g/L HY-Soy, 24 g/L yeast extract and 10 g/L glycerol). The fermentation operating parameters were controlled as follows: temperature set point, 37° C.; pH set point, 7.0 (maintained using 4N ammonium hydroxide and 4N phosphoric acid), and; dissolved oxygen (DO) initially calibrated to 100%. The vessel head pressure was 7 psi, and the agitation and airflow were 200-400 rpm with one volume of air per volume of medium per minute (vvm or slpm), respectively. DO was maintained above 20% by adjusting the fermentation set point parameters in the following priority: Agitation (max 400 rpm), aeration (max 1.5 vvm), oxygen supplementation (max 33.3 lpm), and backpressure (max 12 psi). Foaming was controlled with Pluronic L-61 (25% v/v). When the OD of the culture reached 10 U/mL a glycerol feed (50% v/v) was initiated at a flowrate of 45 mL/min. When OD reached 40 U/mL, the cells were induced with the addition of IPTG to 0.2 mM final concentration.

3.8 Harvest

After 4 hours post-induction, the fermentor was chilled to 10° C. and the airflow and agitation were reduced to 0.3 vvm and 100 rpm respectively. Foam and pH controls were terminated and backpressure was adjusted to 3 psi. The culture was harvested by continuous centrifugation with a Westfalia CSA 8 continuous centrifuge at 10° C. The centrifuge was operated at 15,000 rpm and a flow rate of 3 liters per min and cell slurries collected.

3.9 Cell Lysis and IB Recovery

The fermentation cell paste (from Section 3.8) was diluted 1:5 with Lysis Buffer (6.1 g/L TrizmaBase (Tris), 3.7 g/L ethylenediaminetetraacetic acid (EDTA), 58.44 g/L NaCl and 10 g/L Triton X-100, pH 8.0) and re-suspended using a hand held homogenizer. The re-suspended cell paste was passed twice through a high-pressure homogenizer (parameters: pressure, 10,000 psig; flow rate, 450 mL/min; and temperature, 15° C.). The homogenised cell lysate was then centrifuged (bucket centrifuge, fixed-angle rotor) at 5,000×g for 20 minutes at 4° C. The supernatant was discarded leaving insoluble (inclusion bodies) TGF-β3. The inclusion body (IB) pellet was re-suspended in Wash Buffer (6.1 g/L Tris and 3.72 g/L EDTA, pH 8.0) using a hand held homogenizer and centrifuged (5,000×g for 20 minutes at 4° C.).

3.10 Inclusion Body Solubilization

The sediment from Section 3.9 was diluted 1:10 with Solubilization Buffer (6.1 g/L Tris, 15.4 g/L DL-dithiothreitol (DTT) and 360.4 g/L urea, pH 8.0) and re-suspended using a hand held homogenizer. The suspension was covered and left stirring for 60-75 minutes, at room temperature to solubilize the inclusion bodies and reduce TGF-β3 to its monomeric form. The pH of the re-suspended pellet was adjusted to pH 9.4-9.6 with NaOH/acetic acid before incubation for a second time for 60-75 minutes.

3.11 Clarification/Ultrafiltration and Diafiltration

Solubilized material from Section 3.10 was clarified, concentrated and dia-filtered in a Tangential Flow Filtration (TFF) system (Millipore). Initial clarification and concentration was achieved with a pre-conditioned clarification TFF membrane (Millipore Pellicon 1000 kDa, regenerated cellulose, screen V). The clarified TGF-β3 was collected in the permeate. Switching to a Ultrafiltration/Diafiltration (UF/DF) membrane (Millipore Pellicon 5 kDa, regenerated cellulose, screen C), the TGF-β3 was then washed in 6 diavolumes of Solubilisation Buffer (6.1 g/L Tris, 15.4 g/L DTT and 360.4 g/L urea, pH 9.5).

3.12 Re-Fold Screening Matrix 1

3.12.1 Methodology

TGF-β3 protein content in the clarified material from Section 1.12 was quantified using the RC DC™ Protein Assay (BioRad) in conjunction with SDS-PAGE, Coomassie Blue Staining and densitometry. The TGF-Beta 3 material was diluted into a series of refold buffers (See Tables 1 and 2). 1 mL samples were taken daily over a 6-day timeline and analyzed under non-reducing conditions using SDS-PAGE. Sample aliquots and Mark 12 molecular weight standards (Invitogen—molecular weight range 2.5-200 kDa) were run on NuPAGE® Novex 12% Bis-Tris Gels, 1.0 mm (Invitrogen) for approximately 40-50 minutes at 120 milliAmps and 200 Volts. The protein samples were then electrophoretically transferred to nitrocellulose membrane (Invitrogen) using a Novex Blotting apparatus (Invitrogen). The membrane was blocked with 5% (w/v) skimmed milk powder, 1% (v/v) polyoxyethylenesorbitan monolaurate (Tween 20; Sigma) in phosphate buffered saline (PBS). The membrane was washed (PBS, 0.1% (v/v) Tween 20) and incubated for 1 hour in primary antibody (Anti-TGF-β3, MAB643 (R&D systems) diluted 1:500 in PBS and 0.1 (v/v) Tween 20). Following incubation with the primary antibody, the nitrocellulose was washed in washing buffer (PBS, 1% (v/v) Tween 20). The nitrocellulose was then incubated for an additional 1 hour in the secondary antibody (Goat anti-mouse IgG conjugated with alkaline phosphatase (Abcam PO397) diluted 1:2000 with PBS, 0.1% (v/v) Tween 20). The membrane was again washed (PBS, 1% (v/v) Tween 20 before developing with Western Blue Stabilized Substrate for Alkaline Phosphatase (Promega).

The MAB 643 antibody detects correctly refolded monomeric and dimeric TGF-Beta 3 species.

3.12.2 Results

Tables 1 and 2 summarise the results obtained testing refolding of TGF-β3 under 50 different experimental conditions The inventors established that the conditions described below (i.e. experimental conditions 12, 19, 36, 37, 42, 43 and 44) produced correctly refolded dimeric TGF-Beta 3.

1. 0.7M 2-(cylcohexylamino) ethanesulfonic acid (CHES), 2 mM reduced glutathione (GSH), 0.4 mM oxidised Glutathione (GSSG), 0.12 mg/mL TGF-Beta 3, pH 9.5 at 2-8° C. (Experimental condition 12).
2. 30 mM Taurodeoxycholate, 0.7M CHES, 2 mM GSH, 0.4 mM GSSG, 0.12 mg/mL TGF-Beta 3, pH 9.5 at 2-8° C. (Experimental condition 19).
3. 1M NDSB-201, 2 mM reduced glutathione (GSH), 2 mM oxidised Glutathione (GSSG), 0.12 mg/mL TGF-Beta 3, pH 9.5 at 2-8° C. (Experimental condition 36).
4. 0.7M CHES, 2 mM reduced glutathione (GSH), 2 mM oxidised Glutathione (GSSG), 0.12 mg/mL TGF-Beta 3, pH 9.5 at 2-8° C. (Experimental condition 37).
5. 30 mM Taurodeoxycholate plus 1M NDSB-221, 2 mM reduced glutathione (GSH), 2 mM oxidised Glutathione (GSSG), 0.12 mg/mL TGF-Beta 3, pH 9.5 at 2-8° C. (Experimental condition 42).
6. 30 mM Taurodeoxycholate plus 0.7M CHES, 2 mM reduced glutathione (GSH), 2 mM oxidised Glutathione (GSSG), 0.12 mg/mL TGF-Beta 3, pH 9.5 at 2-8° C. (Experimental condition 43).
7. 30 mM Taurodeoxycholate, 0.7M CHES, 2 mM GSH, 2 mM GSSG, 0.12 mg/mL TGF-Beta 3, pH 9.5 at 2-8° C. (Experimental condition 44).

By way of example FIG. 10 illustrates the effectiveness of Experimental Condition 12.

TABLE 1

Re-fold Screening Matrix and Results

| Experimental Condition | Temp | Detergent | TGF-Beta 3 conc. | GSH conc. | GSSG Conc. | Presence of correctly folded monomeric TGF-Beta 3 by Western Blot (MAB643) analysis |
|---|---|---|---|---|---|---|
| 1 | 2-8° C. | 100 mM Zwittergent 3-08 | 0.12 mg/mL | 2 mM | 0.4 mM | None detected |
| 2 | 2-8° C. | 40 mM Taurocholate | 0.12 mg/mL | 2 mM | 0.4 mM | None detected |
| 3 | 2-8° C. | 40 mM Big CHAP | 0.12 mg/mL | 2 mM | 0.4 mM | None detected |
| 4 | 2-8° C. | 60 mM Hexyl glucopyranoside | 0.12 mg/mL | 2 mM | 0.4 mM | None detected |
| 5 | 2-8° C. | 0.5% (w/v) ASB-14 | 0.12 mg/mL | 2 mM | 0.4 mM | None detected |
| 6 | 2-8° C. | 0.5% (w/v) DDMAB | 0.12 mg/mL | 2 mM | 0.4 mM | None detected |
| 7 | 2-8° C. | 0.5% (w/v) CTAB | 0.12 mg/mL | 2 mM | 0.4 mM | None detected |
| 8 | 2-8° C. | 0.2% (w/v) SDS | 0.12 mg/mL | 2 mM | 0.4 mM | None detected |

TABLE 1-continued

Re-fold Screening Matrix and Results

| Experimental Condition | Temp | Detergent | TGF-Beta 3 conc. | GSH conc. | GSSG Conc. | Presence of correctly folded monomeric TGF-Beta 3 by Western Blot (MAB643) analysis |
|---|---|---|---|---|---|---|
| 9 | 2-8° C. | 0.1% (w/v) Dodecyl-b-D-maltoside | 0.12 mg/mL | 2 mM | 0.4 mM | None detected |
| 10 | 2-8° C. | 0.1% (w/v) Tween 20 | 0.12 mg/mL | 2 mM | 0.4 mM | None detected |
| 11 | 2-8° C. | 1M NDSB-201 | 0.12 mg/mL | 2 mM | 0.4 mM | None detected |
| 12 | 2-8° C. | 0.7M CHES | 0.12 mg/mL | 2 mM | 0.4 mM | Present |
| 13 | 2-8° C. | 20% (v/v) Sucrose | 0.12 mg/mL | 2 mM | 0.4 mM | None detected |
| 14 | 2-8° C. | 20% (v/v) Glycerol | 0.12 mg/mL | 2 mM | 0.4 mM | None detected |
| 15 | 2-8° C. | 20 mM Zwittergent 3-12 + 0.5M Arginine | 0.12 mg/mL | 2 mM | 0.4 mM | None detected |
| 16 | 2-8° C. | 20 mM Zwittergent 3-08 + 1M NDSB-221 | 0.12 mg/mL | 2 mM | 0.4 mM | None detected |
| 17 | 2-8° C. | 30 mM Taurodeoxycholate + 0.5M Arginine | 0.12 mg/mL | 2 mM | 0.4 mM | None detected |
| 18 | 2-8° C. | 30 mM Taurodeoxycholate + 1M NDSB-221 | 0.12 mg/mL | 2 mM | 0.4 mM | None detected |
| 19 | 2-8° C. | 30 mM Taurodeoxycholate + 0.7M CHES | 0.12 mg/mL | 2 mM | 0.4 mM | Present |
| 20 | 2-8° C. | 0.5M Arginine | 0.12 mg/mL | 2 mM | 0.4 mM | None detected |
| 21 | 2-8° C. | 40 mM Octyl-Thioglucopyranoside | 0.12 mg/mL | 2 mM | 0.4 mM | None detected |
| 22 | 2-8° C. | 60 mM Hexylglucopyranoside + 0.1% (w/v) PEG-6000 | 0.12 mg/mL | 2 mM | 0.4 mM | None detected |
| 23 | 2-8° C. | 30% (v/v) Ethanol | 0.12 mg/mL | 2 mM | 0.4 mM | None detected |
| 24 | 2-8° C. | 20% (v/v) Isopropyl Alcohol | 0.12 mg/mL | 2 mM | 0.4 mM | None detected |
| 25 | 2-8° C. | 30 mM Taurodeoxycholate | 0.12 mg/mL | 2 mM | 0.4 mM | None detected |

TABLE 2

Re-fold Screening Matrix and Results

| Experimental Condition | Temp | Detergent | TGF-Beta 3 conc. | GSH conc. | GSSG Conc. | Presence of correctly folded monomeric TGF-Beta 3 by Western Blot (MAB643) analysis |
|---|---|---|---|---|---|---|
| 26 | 2-8° C. | 100 mM Zwittergent 3-08 | 0.12 mg/mL | 2 mM | 2 mM | None detected |
| 27 | 2-8° C. | 40 mM Taurocholate | 0.12 mg/mL | 2 mM | 2 mM | None detected |
| 28 | 2-8° C. | 40 mM Big CHAP | 0.12 mg/mL | 2 mM | 2 mM | None detected |
| 29 | 2-8° C. | 60 mM Hexyl glucopyranoside | 0.12 mg/mL | 2 mM | 2 mM | None detected |
| 30 | 2-8° C. | 0.5% (w/v) ASB-14 | 0.12 mg/mL | 2 mM | 2 mM | None detected |
| 31 | 2-8° C. | 0.5% (w/v) DDMAB | 0.12 mg/mL | 2 mM | 2 mM | None detected |
| 32 | 2-8° C. | 0.5% (w/v) CTAB | 0.12 mg/mL | 2 mM | 2 mM | None detected |
| 33 | 2-8° C. | 0.2% (w/v) SDS | 0.12 mg/mL | 2 mM | 2 mM | None detected |
| 34 | 2-8° C. | 0.1% (w/v) Dodecyl-b-D-maltoside | 0.12 mg/mL | 2 mM | 2 mM | None detected |
| 35 | 2-8° C. | 0.1% (w/v) Tween 20 | 0.12 mg/mL | 2 mM | 2 mM | None detected |
| 36 | 2-8° C. | 1M NDSB-201 | 0.12 mg/mL | 2 mM | 2 mM | Present |
| 37 | 2-8° C. | 0.7M CHES | 0.12 mg/mL | 2 mM | 2 mM | Present |
| 38 | 2-8° C. | 20% (v/v) Sucrose | 0.12 mg/mL | 2 mM | 2 mM | None detected |
| 39 | 2-8° C. | 20% (v/v) Glycerol | 0.12 mg/mL | 2 mM | 2 mM | None detected |
| 40 | 2-8° C. | 20 mM Zwittergent 3-12 + 0.5M Arginine | 0.12 mg/mL | 2 mM | 2 mM | None detected |
| 41 | 2-8° C. | 20 mM Zwittergent 3-08 + 1M NDSB-221 | 0.12 mg/mL | 2 mM | 2 mM | None detected |

TABLE 2-continued

Re-fold Screening Matrix and Results

| Experimental Condition | Temp | Detergent | TGF-Beta 3 conc. | GSH conc. | GSSG Conc. | Presence of correctly folded monomeric TGF-Beta 3 by Western Blot (MAB643) analysis |
|---|---|---|---|---|---|---|
| 42 | 2-8° C. | 30 mM Taurodeoxycholate + 0.5M Arginine | 0.12 mg/mL | 2 mM | 2 mM | Present |
| 43 | 2-8° C. | 30 mM Taurodeoxycholate + 1M NDSB-221 | 0.12 mg/mL | 2 mM | 2 mM | Present |
| 44 | 2-8° C. | 30 mM Taurodeoxycholate + 0.7M CHES | 0.12 mg/mL | 2 mM | 2 mM | Present |
| 45 | 2-8° C. | 0.5M Arginine | 0.12 mg/mL | 2 mM | 2 mM | None detected |
| 46 | 2-8° C. | 40 mM Octyl-Thioglucopyranoside | 0.12 mg/mL | 2 mM | 2 mM | None detected |
| 47 | 2-8° C. | 60 mM Hexylglucopyranoside + 0.1% (w/v) PEG-6000 | 0.12 mg/mL | 2 mM | 2 mM | None detected |
| 48 | 2-8° C. | 30% (v/v) Ethanol | 0.12 mg/mL | 2 mM | 2 mM | None detected |
| 49 | 2-8° C. | 20% (v/v) Isopropyl Alcohol | 0.12 mg/mL | 2 mM | 2 mM | None detected |
| 50 | 2-8° C. | 30 mM Taurodeoxycholate | 0.12 mg/mL | 2 mM | 2 mM | None detected |

3.13 Ultrafiltration/Hydrophobic Interaction Chromatography

The selected refolding solution was concentrated 5 fold by ultrafiltration (the membrane was a flat-sheet Millipore Pellicon 5 kDa, 0.1 m², Regenerated Cellulose, screen). The pH of the concentrated re-fold material was then adjusted to a pH of 2.5-2.8 using glacial acetic acid before being diluted 1:1 in Dilution Buffer (2.72 g/L sodium acetate, 264.28 g/L ammonium sulfate, 100 g/L acetic acid, and 210.7 g/L arginine hydrochloride pH 3.3). A Butyl Sepharose 4 Fast Flow Column (Amersham, 16 cm Bed Height) was equilibrated with four column volumes of Buffer A (2.72 g/L sodium acetate, 132.14 g/L ammonium sulfate and 100 g/L acetic acid pH 3.3). The refold material was filtered through 0.22 μM membrane (Millipore Millipak filter) before being loaded onto the Butyl Sepharose column at a flow rate of 100 cm/hr (this flow rate was used throughout procedure). The column was then washed in Buffer A for four-column volumes. The TGF-Beta 3 proteins were eluted off the column using Buffer B (2.72 g/L sodium acetate, 100 g/L acetic acid and 300 g/L ethanol pH 3.3). The first peak, which contains TGF-β3 proteins in both monomeric and dimeric forms, was pooled (see FIG. 11), prior to separation of the monomeric proteins.

Sequence Information
TGF-β1 (Sequence ID No. 1)
ALDTNYCFSSTEKNCCVRQLYIDFRKDLGWKWIHEPKGYHANFCLGPCPY

IWSLDTQYSKVLALYNQHNPGASAAPCCVPQALEPLPIVYYVGRKPKVEQ

LSNMIVRSCKCS

TGF-β2 (Sequence ID No. 2)
ALDAAYCFRNVQDNCCLRPLYIDFKRDLGWKWIHEPKGYNANFCAGACPY

LWSSDTQHSRVLSLYNTINPEASASPCCVSQDLEPLTILYYIGKTPKIEQ

LSNMIVKSCKCS

TGF-β3 (Sequence ID No. 3)
ALDTNYCFRNLEENCCVRPLYIDFRQDLGWKWVHEPKGYYANFCSGPCPY

LRSADTTHSTVLGLYNTLNPEASASPCCVPQDLEPLTILYYVGRTPKVEQ

LSNMVVKSCKCS

DNA encoding full-length TGF-Beta 1 (Sequence ID No. 4), showing signal peptide (shown in italics), pro-peptide (shown in bold) as well as the active fragment (shown in normal text)

*atgccgccct ccgggctgcg gctgctgctg ctgctgctac cgctgctgtg gctactggtg*

*ctgacgcctg gccggccggc cgcgggacta* tccacctgca agactatcga catggagctg gtgaagcgga agcgcatcga ggccatccgc ggccagatcc tgtccaagct gcggctcgcc agcccccga gccagggga ggtgccgccc ggcccgctgc ccgaggccgt gctcgccctg tacaacagca cccgcgaccg ggtggccggg gagagtgcag aaccggagcc cgagcctgag gccgactact acgccaagga ggtcacccgc gtgctaatgg tggaaaccca caacgaaatc tatgacaagt tcaagcagag tacacacagc atatatatgt tcttcaacac atcagagctc cgagaagcgg tacctgaacc cgtgttgctc tcccgggcag agctgcgtct gctgaggctc aagttaaaag tggagcagca cgtggagctg taccagaaat acagcaacaa ttcctggcga tacctcagca accggctgct ggcacccagc gactcgccag agtggttatc ttttgatgtc

```
accggagttg tgcggcagtg gttgagccgt ggaggggaaa ttgagggctt tcgccttagc gcccactgct cctgtgacag cagggataac acactgcaag tggacatcaa cgggttcact accggccgcc gaggtgacct ggccaccatt catggcatga accggccttt cctgcttctc atggccaccc cgctggagag ggcccagcat ctgcaaagct cccggcaccg ccgagccctg gacaccaact attgcttcag ctccacggag aagaactgct gcgtgcggca gctgtacatt gacttccgca aggacctcgg ctggaagtgg atacacgaga ccaagggcta ccatgccaac ttctgcctcg ggccctgccc ctacatttgg agcctggaca cgcagtacag caaggtcctg gccctgtaca accagcataa cccgggcgcc taggaggaga cgtgctgcgt gccgcaggcg ctggagccgc tgcccathgt gtactacgtg ggccgcaagc ccaaggtgga gcagctgtcc aacatgatcg tgcgctcctg caagtgcagc tga
```

DNA encoding full-length TGF-Beta 2 (Sequence ID No. 5), showing signal peptide (shown in italics), pro-peptide (shown in bold) as well as the active fragment (shown in normal text)

*ctgtctacct gcagcacact cgatatggac cagttcatgc gcaagaggat* cgaggcgatc cgcgggcaga tcctgagcaa gctgaagctc accagtcccc cagaagacta tcctgagccc gaggaagtcc ccccggaggt gatttccatc tacaacagca ccagggactt gctccaggag aaggcgagcc ggagggcggc cgcctgcgag cgcgagagga gcgacgaaga gtactacgcc aaggaggttt acaaaataga catgccgccc ttcttcccct ccgaagccat cccgcccact ttctacagac cctacttcag aattgttcga tttgacgtct cagcaatgga gaagaatgct tccaatttgg tgaaagcaga gttcagagtc tttcgtttgc agaacccaaa agccagagtg cctgaacaac ggattgagct atatcagatt ctcaagtcca aagatttaac atctccaacc cagcgctaca tcgacagcaa agttgtgaaa acaagagcag aaggcgaatg gctctccttc gatgtaactg atgctgttca tgaatggctt caccataaag acaggaacct gggatttaaa ataagcttac actgtccctg ctgcactttt gtaccatcta ataattacat catcccaaat aaaagtgaag aactagaagc aagatttgca ggtattgatg gcacctccac atataccagt ggtgatcaga aaactataaa gtccactagg aaaaaaaaca gtgggaagac cccacatctc ctgctaatgt tattgccctc ctacagactt gagtcacaac agaccaaccg gcggaagaag cgtgctttgg atgcggccta ttgctttaga aatgtgcagg ataattgctg cctacgtcca ctttacattg atttcaagag ggatctaggg tggaaatgga tacacgaacc caaagggtac aatgccaact tctgtgctgg agcatgcccg tatttatgga gttcagacac tcagcacaga agggtcctga gcttatataa taccataaat ccagaagcat ctgcttctcc ttgctgcgtg tcccaaqatt tagaacctct aaccattctc tactacattg gcaaaacacc caagattgaa cagctttcta atatgattgt aaagtcttgc aaatgcagct aa DNA encoding full-length TGF-Beta 3 (Sequence ID No. 6), showing signal peptide (shown in italics), pro-peptide (shown in bold) as well as the active fragment (shown in normal text)

*atgaagatgc acttgcaaag ggctctggtg gtcctggccc tgctgaactt tgccacggtc* 60 agcctctctc tgtccacttg caccaccttg gacttcggcc acatcaagaa gaagagggtg 120
gaagccatta ggggacagat cttgagcaag ctcaggctca ccagcccccc tgagccaacg 180

```
gtgatgaccc acgtccccta tcaggtcctg gccctttaca acagcacccg ggagctgctg    240
gaggagatgc atgggagag ggaggaaggc tgcacccagg aaaacaccga gtcggaatac     300
tatgccaaag aaatccataa attcgacatg atccaggggc tggcggagca caacgaactg    360
gctgtctgcc ctaaaggaat tacctccaag gttttccgct tcaatgtgtc ctcagtggag    420
aaaaatagaa ccaacctatt ccgagcagaa ttccgggtct tgcgggtgcc caaccccagc    480
tctaagcgga atgagcagag gatcgagctc ttccagatcc ttcggccaga tgagcacatt    540
gccaaacagc gctatatcgg tggcaagaat ctgcccacac ggggcactgc cgagtggctg    600
tcctttgatg tcactgacac tgtgcgtgag tggctgttga agagagagtc caacttaggt    660
ctagaaatca gcattcactg tccatgtcac acctttcagc ccaatggaga tatcctggaa    720
aacattcacg aggtgatgga aatcaaattc aaaggcgtgg acaatgagga tgaccatggc    780
cgtggagatc tggggcgcct caagaagcag aaggatcacc acaaccctca tctaatcctc    840
atgatgattc ccccacaccg gctcgacaac ccgggccagg ggggtcagag gaagaagcgg    900
gctttggaca ccaattactg cttccgcaac ttggaggaga actgctgtgt gcgccccctc    960
tacattgact ccgacagga tctgggctgg aagtgggtcc atgaacctaa gggctactat   1020
gccaacttct gctcaggccc ttgcccatac ctccgcagtg cagacacaac ccacagcacg   1080
gtgctgggac tgtacaacac tctgaaccct gaagcatctg cctcgccttg ctgcgtgccc   1140
caggacctgg agccctgac catcctgtac tatgttggga ggaccccaa agtggagcag    1200 ctctccaaca tggtggtgaa gtcttgtaaa tgtagctga
```

Sequence ID No. 7—DNA Encoding Active Fragment of Wild-Type Human TGF-β3

```
GCT TTG GAC ACC AAT TAC TGC TTC CGC AAC TTG GAG
GAG AAC TGC TGT GTG CGC CCC CTC TAC ATT GAC TTC
CGA CAG GAT CTG GGC TGG AAG TGG GTC CAT GAA CCT
AAG GGC TAC TAT GCC AAC TTC TGC TCA GGC CCT TGC
CCA TAC CTC CGC AGT GCA GAC ACA ACC CAC AGC ACG
GTG CTG GGA CTG TAC AAC ACT CTG AAC CCT GAA GCA
TCT GCC TCG CCT TGC TGC GTG CCC CAG GAC CTG GAG
CCC CTG ACC ATC CTG TAC TAT GTT GGG AGG ACC CCC
AAA GTG GAG CAG CTC TCC AAC ATG GTG GTG AAG TCT
TGT AAA TGT AGC
```

Sense and Antisense Primers for the cDNA Generation of TGF-Beta 1, TGF-Beta 2 and TGF-Beta 3:

TGF-Beta 1
Sense primer-5'
GTT ACA CCA TGG CCC TGG ACA CCA ACT ATT 3'

Anti-Sense primer-3'
CAG CCG GAT CCG GTC GAC TCA GCT GCA CTT 5'

TGF-Beta 2
Sense primer-5'
GTT ACA CCA TGG CTT TGG ATG CGG CCT ATT

Anti-Sense primer-3'
CAG CCG GAT CC G GTC GAC TCA GCT GCA TTT G 5'

TGF-Beta 3
Sense primer-5'
GAT ATA CCA TGG CTT TGG ACA CCA ATT ACT ACT GC 3'

Anti-Sense primer-5'
CAG CCG GAT CCG GTC GAC TCA GCT ACA TTT ACA AGA C 3'

---

The invention claimed is:

1. A method of accelerating wound healing, the method comprising administering to a patient in need of such treatment a therapeutically effective amount of a monomeric wild-type TGF-β3 or a biologically active fragment thereof to accelerate healing of a wound.

2. A method according to claim 1, wherein the monomeric wild-type TGF-β3 is administered and the monomeric wild-type TGF-β3 has an amino acid sequence comprising Sequence ID No. 3.

3. A method according to claim 1 wherein the wound is a dermal wound.

4. A method according to claim 1 wherein the wound is an acute wound.

5. A method according to claim 1 wherein the wound is a burn.

6. A method according to claim 1 wherein the wound is a chronic wound.

7. A method for promoting epithelial regeneration while inhibiting scarring, the method comprising administering to a patient in need thereof a therapeutically effective amount of a monomeric wild-type TGF-β3 or a biologically active fragment thereof to promote epithelial regeneration and inhibit scarring.

8. A method according to claim 7 wherein the epithelial regeneration occurs at a site of damaged epithelium.

9. A method according to claim 8 wherein the epithelia is epidermis.

10. A method of inhibiting scarring, the method comprising administering to a patient in need of such treatment a therapeutically effective amount of a monomeric wild-type TGF-β3 or a biologically active fragment thereof to inhibit scarring.

11. A method according to claim 10, wherein wild-type TGF-β3 monomer having an amino acid sequence comprising Sequence ID No. 3 is administered.

12. A method according to claim 10 wherein the inhibition of scarring is effected at the dermis.

13. A method according to claim 10 inhibition of scarring is effected at the site of an acute wound.

14. A method according to claim 13 wherein the wound is a burn.

15. A method according to claim 10 wherein the inhibition of scarring is effected at the site of a chronic wound.

16. A method according to claim 7, wherein wild type TGF-β3 monomer having an amino acid sequence comprising Sequence ID No. 3 is administered.

17. A method of accelerating wound healing while inhibiting scarring, the method comprising administering to a patient in need of such treatment a therapeutically effective amount of a monomeric wild-type TGF-β or a biologically active fragment thereof to accelerate wound healing and inhibit scarring.

18. A method according to claim 17, wherein wild-type TGF-β3 monomer having an amino acid sequence comprising Sequence ID No. 3 is administered.

19. A method according to claim 1, wherein 50-200 ng of the monomeric wild-type TGF-β3 or biologically active fragment thereof/linear cm of wound is administered.

20. A method according to claim 1, wherein 100-300 ng of the monomeric wild-type TGF-β3 or biologically active fragment thereof/linear cm of wound is administered.

21. A method according to claim 7, wherein 50-200 ng of the monomeric wild-type TGF-β3 or biologically active fragment thereof/cm$^2$ of epithelial damage is administered.

22. A method according to claim 7, wherein 100-300 ng of the monomeric wild-type TGF-β3 or biologically active fragment thereof/cm$^2$ of epithelial damage is administered.

23. A method according to claim 10, wherein 50-200 ng of the monomeric wild-type TGF-β3 or biologically active fragment thereof/linear cm of wound is administered.

24. A method according to claim 10, wherein 100-300 ng of the monomeric wild-type TGF-β3 or biologically active fragment thereof/linear cm of wound is administered.

25. A method according to claim 17, wherein 50-200 ng of the monomeric wild-type TGF-β3 or biologically active fragment thereof/linear cm of wound is administered.

26. A method according to claim 17, wherein 100-300 ng monomeric of the wild-type TGF-β3 or biologically active fragment thereof/linear cm of wound is administered.

27. A method according to claim 1, wherein the TGF-β3 or biologically active fragment thereof is administered (a) immediately prior to formation of a wound and (b) again 24 hours after wounding.

28. A method according to claim 1, wherein the TGF-β3 or biologically active fragment thereof is administered once a day for up to 3 days.

29. A method according to claim 1, wherein the TGF-β3 or biologically active fragment thereof is administered immediately prior to the forming of the wound.

30. The method according to claim 1, wherein the biologically active fragment of TGF-β3 comprises the receptor-binding portion of TGF-β3.

31. The method according to claim 1, wherein the biologically active fragment of TGF-β3 has wound healing activity in a rat model of cutaneous wound healing.

32. A method of accelerating wound healing, the method comprising administering by injection to a patient in need thereof 50-200 ng of monomeric wild-type TGF-β3 /linear cm of wound immediately prior to the forming of a wound to accelerate healing of the wound.

33. A method for promoting epithelial regeneration while inhibiting scarring, the method comprising administering by injection to a patient in need thereof 50-200 ng of monomeric wild-type TGF-β3/cm$^2$ of epithelial damage immediately prior to the forming of a wound to the patient to promote epithelial regeneration and inhibit scarring.

34. A method of inhibiting scarring, the method comprising administering by injection to a patient in need thereof 50-200 ng of monomeric wild-type TGF-β3/cm$^2$ of epithelial damage immediately prior to the forming of a wound to the patient to inhibit scarring.

35. A method of accelerating wound healing, the method comprising administering by injection to a patient in need thereof (a) immediately prior to formation of a wound and (b) again 24 hours after wounding, a therapeutically effective amount of monomeric wild-type TGF-β3 to accelerate healing of the wound.

36. A method for promoting epithelial regeneration while inhibiting scarring, the method comprising administering by injection to a patient in need thereof (a) immediately prior to formation of a wound and (b) again 24 hours after wounding, a therapeutically effective amount of monomeric wild-type TGF-β3 to promote epithelial regeneration and inhibit scarring.

37. A method of inhibiting scarring, the method comprising administering by injection to a patient in need thereof (a) immediately prior to formation of a wound and (b) again 24 hours after wounding, a therapeutically effective amount of monomeric wild-type TGF-β3 to inhibit scarring.

* * * * *

SEQUENCE LISTING

<160> NUMBER OF SEQ ID NOS: 15

<210> SEQ ID NO 1
<211> LENGTH: 112
<212> TYPE: PRT
<213> ORGANISM: Homo sapiens

<400> SEQUENCE: 1

```
Ala Leu Asp Thr Asn Tyr Cys Phe Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 2
<211> LENGTH: 112
<212> TYPE: PRT
<213> ORGANISM: Homo sapiens

<400> SEQUENCE: 2

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Arg Val Leu Ser Leu
        50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 3
<211> LENGTH: 112
<212> TYPE: PRT
<213> ORGANISM: Homo sapiens

<400> SEQUENCE: 3

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 4
<211> LENGTH: 1173
<212> TYPE: DNA
<213> ORGANISM: Homo sapiens

<400> SEQUENCE: 4

```
atgccgccct ccgggctgcg gctgctgctg ctgctgctac cgctgctgtg gctactggtg      60
ctgacgcctg gccggccggc cgcgggacta tccacctgca agactatcga catggagctg     120
gtgaagcgga agcgcatcga ggccatccgc ggccagatcc tgtccaagct gcggctcgcc     180
agccccccga gccaggggga ggtgccgccc ggccgctgc cgaggccgt gctcgccctg       240
tacaacagca cccgcgaccg ggtggccggg agagtgcag aaccggagcc cgagcctgag      300
gccgactact acgccaagga ggtcaccgc gtgctaatgg tggaaaccca caacgaaatc      360
tatgacaagt tcaagcagag tacacacagc atatatatgt tcttcaacac atcagagctc    420
cgagaagcgg tacctgaacc cgtgttgctc tcccgggcag agctgcgtct gctgaggctc     480
aagttaaaag tggagcagca cgtggagctg taccagaaat acagcaacaa ttcctggcga    540
tacctcagca accggctgct ggcacccagc gactcgccag agtggttatc ttttgatgtc    600
accggagttg tgcggcagtg gttgagccgt ggaggggaaa ttgagggctt cgccttagc     660
gcccactgct cctgtgacag cagggataac acactgcaag tggacatcaa cgggttcact   720
accggccgcc gaggtgacct ggccaccatt catggcatga accggccttt cctgcttctc     780
atggccaccc cgctggagag ggcccagcat ctgcaaagct cccggcaccg ccgagccctg     840
gacaccaact attgcttcag ctccacggag aagaactgct gcgtgcggca gctgtacatt    900
gacttccgca aggacctcgg ctggaagtgg atccacgagc ccaagggcta ccatgccaac     960
ttctgcctcg ggccctgccc ctacatttgg agcctggaca cgcagtacag caaggtcctg   1020
gccctgtaca accagcataa cccgggcgcc tcggcggcgc cgtgctgcgt gccgcaggcg   1080
ctggagccgc tgcccathgt gtactacgtg ggccgcaagc ccaaggtgga gcagctgtcc   1140
aacatgatcg tgcgctcctg caagtgcagc tga                                 1173
```

<210> SEQ ID NO 5
<211> LENGTH: 1182
<212> TYPE: DNA
<213> ORGANISM: Homo sapiens

<400> SEQUENCE: 5

```
ctgtctacct gcagcacact cgatatggac cagttcatgc gcaagaggat cgaggcgatc      60
cgcgggcaga tcctgagcaa gctgaagctc accagtcccc cagaagacta tcctgagccc    120
gaggaagtcc ccccggaggt gatttccatc tacaacagca ccaggacttt gctccaggag    180
aaggcgagcc ggagggcggc cgcctgcgag cgcgagagga gcgacgaaga gtactacgcc    240
aaggaggttt acaaaataga catgccgccc ttcttcccct ccgaagccat cccgcccact    300
ttctacagac cctacttcag aattgttcga tttgacgtct cagcaatgga agaatgct      360
tccaatttgg tgaaagcaga gttcagagtc tttcgtttgc agaacccaaa agccagagtg   420
cctgaacaac ggattgagct atatcagatt ctcaagtcca agatttaac atctccaacc    480
cagcgctaca tcgacagcaa agttgtgaaa acaagagcag aaggcgaatg gctctccttc   540
gatgtaactg atgctgttca tgaatggctt caccataaag acaggaacct gggatttaaa   600
ataagcttac actgtcctg ctgcacttttt gtaccatcta ataattacat catcccaaat    660
aaaagtgaag aactagaagc aagatttgca ggtattgatg gcacctccac atataccagt   720
```

```
ggtgatcaga aaactataaa gtccactagg aaaaaaaaca gtgggaagac cccacatctc      780
ctgctaatgt tattgccctc ctacagactt gagtcacaac agaccaaccg gcggaagaag      840
cgtgctttgg atgcggccta ttgctttaga aatgtgcagg ataattgctg cctacgtcca      900
ctttacattg atttcaagag ggatctaggg tggaaatgga tacacgaacc caagggtac       960 aatgccaact tctgtgctgg agcatgcccg tatttatgga gttcagacac tcagcacagc     1020
agggtcctga gctatataaa taccataaat ccagaagcat ctgcttctcc ttgctgcgtg     1080
tcccaagatt tagaacctct aaccattctc tactacattg gcaaacacc caagattgaa      1140 cagctttcta atatgattgt aaagtcttgc aaatgcagct aa                        1182

<210> SEQ ID NO 6
<211> LENGTH: 1239
<212> TYPE: DNA
<213> ORGANISM: Homo sapiens

<400> SEQUENCE: 6
atgaagatgc acttgcaaag ggctctggtg gtcctggccc tgctgaactt tgccacggtc       60
agcctctctc tgtccacttg caccaccttg gacttcggcc acatcaagaa gaagagggtg      120
gaagccatta ggggacagat cttgagcaag ctcaggctca ccagcccccc tgagccaacg      180
gtgatgaccc acgtccccta tcaggtcctg gccctttaca acagcacccg ggagctgctg      240
gaggagatgc atggggagag ggaggaaggc tgcacccagg aaaacaccga gtcggaatac      300
tatgccaaag aaatccataa attcgacatg atccaggggc tggcggagca caacgaactg      360
gctgtctgcc ctaaaggaat tacctccaag gttttccgct tcaatgtgtc ctcagtggag      420
aaaaatagaa ccaacctatt ccgagcagaa ttccgggtct tgcgggtgcc caaccccagc      480
tctaagcgga atgagcagag gatcgagctc ttccagatcc ttcggccaga tgagcacatt      540
gccaaacagc gctatatcgg tggcaagaat ctgcccacac ggggcactgc cgagtggctg      600
tcctttgatg tcactgacac tgtgcgtgag tggctgttga agagagagtc caacttaggt      660
ctagaaatca gcattcactg tccatgtcac acctttcagc ccaatggaga tatcctggaa      720
aacattcacg aggtgatgga aatcaaattc aaaggcgtgg acaatgagga tgaccatggc      780
cgtggagatc tggggcgcct caagaagcag aaggatcacc acaaccctca tctaatcctc      840
atgatgattc cccacaccg gctcgacaac ccgggccagg ggggtcagag gaagaagcgg      900
gctttggaca ccaattactg cttccgcaac ttggaggaga actgctgtgt gcgcccccte      960 tacattgact ccgacagga tctgggctgg aagtgggtcc atgaacctaa gggctactat     1020
gccaacttct gctcaggccc ttgcccatac ctccgcagtg cagacacaac ccacagcacg     1080
gtgctgggac tgtacaacac tctgaaccct gaagcatctg cctcgccttg ctgcgtgccc     1140
caggacctgg agccctgac catcctgtac tatgttggga ggaccccaa agtggagcag      1200 ctctccaaca tggtggtgaa gtcttgtaaa tgtagctga                            1239

<210> SEQ ID NO 7
<211> LENGTH: 336
<212> TYPE: DNA
<213> ORGANISM: Homo sapiens

<400> SEQUENCE: 7
gctttggaca ccaattactg cttccgcaac ttggaggaga actgctgtgt gcgcccccte       60 tacattgact ccgacagga tctgggctgg aagtgggtcc atgaacctaa gggctactat       120
gccaacttct gctcaggccc ttgcccatac ctccgcagtg cagacacaac ccacagcacg      180
```

```
gtgctgggac tgtacaacac tctgaaccct gaagcatctg cctcgccttg ctgcgtgccc    240
caggacctgg agccctgac catcctgtac tatgttggga ggaccccaa agtggagcag     300 ctctccaaca tggtggtgaa gtcttgtaaa tgtagc                              336
```

```
<210> SEQ ID NO 8
<211> LENGTH: 30
<212> TYPE: DNA
<213> ORGANISM: Artificial
<220> FEATURE:
<223> OTHER INFORMATION: Sense primer for TGF-beta 1

<400> SEQUENCE: 8
gttacaccat ggccctggac accaactatt                                     30

<210> SEQ ID NO 9
<211> LENGTH: 30
<212> TYPE: DNA
<213> ORGANISM: Artificial
<220> FEATURE:
<223> OTHER INFORMATION: Antisense primer for TGF-beta 1

<400> SEQUENCE: 9
cagccggatc cggtcgactc agctgcactt                                     30

<210> SEQ ID NO 10
<211> LENGTH: 30
<212> TYPE: DNA
<213> ORGANISM: Artificial
<220> FEATURE:
<223> OTHER INFORMATION: Sense primer for TGF-beta 2

<400> SEQUENCE: 10
gttacaccat ggctttggat gcggcctatt                                     30

<210> SEQ ID NO 11
<211> LENGTH: 31
<212> TYPE: DNA
<213> ORGANISM: Artificial
<220> FEATURE:
<223> OTHER INFORMATION: Antisense primer for TGF-beta 2

<400> SEQUENCE: 11
cagccggatc cggtcgactc agctgcattt g                                   31

<210> SEQ ID NO 12
<211> LENGTH: 35
<212> TYPE: DNA
<213> ORGANISM: Artificial
<220> FEATURE:
<223> OTHER INFORMATION: Sense primer for TGF-beta 3

<400> SEQUENCE: 12
gatataccat ggctttggac accaattact actgc                               35

<210> SEQ ID NO 13
<211> LENGTH: 37
<212> TYPE: DNA
<213> ORGANISM: Artificial
<220> FEATURE:
<223> OTHER INFORMATION: Antisense primer for TGF-beta 3

<400> SEQUENCE: 13
cagccggatc cggtcgactc agctacattt acaagac                             37

<210> SEQ ID NO 14
```

```
<211> LENGTH: 20
<212> TYPE: DNA
<213> ORGANISM: Artificial
<220> FEATURE:
<223> OTHER INFORMATION: T7 promoter primer

<400> SEQUENCE: 14
taatacgact cactataggg                                              20

<210> SEQ ID NO 15
<211> LENGTH: 19
<212> TYPE: DNA
<213> ORGANISM: Artificial
<220> FEATURE:
<223> OTHER INFORMATION: T7 terminator primer

<400> SEQUENCE: 15
gctagttatt gctcagcgg                                               19
```